US010597751B2

(12) United States Patent
Wang et al.

(10) Patent No.: US 10,597,751 B2
(45) Date of Patent: Mar. 24, 2020

(54) LIGAND ASSISTED CHROMATOGRAPHY FOR METAL ION SEPARATION

(71) Applicant: Purdue Research Foundation, West Lafayette, IN (US)

(72) Inventors: Nien-Hwa Linda Wang, West Lafayette, IN (US); Lei Ling, Devens, MA (US)

(73) Assignee: Purdue Research Foundation, West Lafayette, IN (US)

( * ) Notice: Subject to any disclaimer, the term of this patent is extended or adjusted under 35 U.S.C. 154(b) by 432 days.

(21) Appl. No.: 15/327,041

(22) PCT Filed: Jul. 17, 2015

(86) PCT No.: PCT/US2015/040975
§ 371 (c)(1),
(2) Date: Jan. 18, 2017

(87) PCT Pub. No.: WO2016/011396
PCT Pub. Date: Jan. 21, 2016

(65) Prior Publication Data
US 2017/0166993 A1  Jun. 15, 2017

Related U.S. Application Data

(60) Provisional application No. 62/026,487, filed on Jul. 18, 2014.

(51) Int. Cl.
*C22B 3/20* (2006.01)
*B01D 15/38* (2006.01)
(Continued)

(52) U.S. Cl.
CPC .......... *C22B 3/0098* (2013.01); *B01D 15/166* (2013.01); *B01D 15/1871* (2013.01);
(Continued)

(58) Field of Classification Search
CPC .... B01D 15/361; B01D 15/362; B01D 15/38; B01D 15/3804; B01D 15/3828;
(Continued)

(56) References Cited

U.S. PATENT DOCUMENTS 2,798,789 A * 7/1957 Spedding ............ C01F 17/0006
423/21.5
3,033,646 A * 5/1962 Hansen ............... C01F 17/0006
423/21.5
(Continued)

OTHER PUBLICATIONS

American Elements, "Samarium Metal," available at <https://www.americanelements.com/sm.html>, dated May 1, 2012, accessed Mar. 22, 2019, 9 pgs. (Year: 2012).*
(Continued)

*Primary Examiner* — Katherine Zalasky McDonald
(74) *Attorney, Agent, or Firm* — Purdue Research Foundation; Liang Zeng Yan

(57) ABSTRACT

Presented herein is a ligand-assisted elution chromatography process for the separation of metal ions using a sorbent. In particular, the present invention discloses a process of two sets of column system in combination with two sets of eluting ligand solutions to prepare substantially pure rare earth elements, wherein the first set of column comprises strong acid cation exchange resins and the second set of chromatographic columns comprises hydrous polyvalent metal oxide selected from the group consisting of $TiO_2$, $ZrO_2$, or $SnO_2$ and wherein ligand of said second ligand solution coordinates with said hydrous polyvalent metal oxide.

11 Claims, 17 Drawing Sheets

(51) Int. Cl.
*B01D 15/16* (2006.01)
*B01D 15/18* (2006.01)
*B01D 15/36* (2006.01)
*B01D 15/42* (2006.01)
*C22B 3/24* (2006.01)
*C22B 59/00* (2006.01)
*G01N 30/46* (2006.01)
*C22B 3/06* (2006.01)

(52) U.S. Cl.
CPC ....... *B01D 15/362* (2013.01); *B01D 15/3828* (2013.01); *B01D 15/42* (2013.01); *C22B 3/06* (2013.01); *C22B 3/24* (2013.01); *C22B 59/00* (2013.01); *G01N 30/461* (2013.01); *G01N 30/463* (2013.01); *B01D 15/422* (2013.01); *B01D 2015/3838* (2013.01); *Y02P 10/234* (2015.11)

(58) Field of Classification Search
CPC .. B01D 15/422; B01D 15/426; B01D 15/265; B01D 2015/3838; G01N 30/38; G01N 30/46; G01N 30/461; G01N 30/462; G01N 30/463; C22B 3/0098; C22B 3/42; C22B 59/00
See application file for complete search history.

(56) References Cited

U.S. PATENT DOCUMENTS

| | | | | |
|---|---|---|---|---|
| 3,228,750 | A | * | 1/1966 | Lindstrom .......... C01F 17/0006 423/21.5 |
| 3,615,173 | A | * | 10/1971 | Winget ................ C22B 59/00 423/21.5 |
| 4,411,793 | A | * | 10/1983 | Kato .................... B01D 15/08 210/656 |
| 4,514,367 | A | * | 4/1985 | Asami ................... B01J 47/12 423/21.5 |
| 4,816,233 | A | * | 3/1989 | Rourke ............. C01F 17/0006 210/672 |
| 5,182,251 | A | * | 1/1993 | Bruening ........... B01J 20/3259 502/401 |
| 2011/0182786 | A1 | * | 7/2011 | Burba, III ................ C22B 3/02 423/20 |

OTHER PUBLICATIONS

Sigma-Aldrich, "Practical considerations for IEX separation," Extracted from Ion Exchange Chromatography & Chromatofocusing, GE Healthcare, 2007, 14 pages. (Year: 2007).*

* cited by examiner

LIGAND ASSISTED CHROMATOGRAPHY FOR METAL ION SEPARATION

CROSS-REFERENCE TO RELATED APPLICATIONS

The present patent application is a national stage entry under 35 U.S.C. § 371(c) of International Application No. PCT/US2015/040975, filed on Jul. 17, 2015, which claims priority under 35 U.S.C. § 119(e) to U.S. Provisional Patent Application Ser. No. 62/026,487, filed on Jul. 18, 2014, the contents of which are hereby incorporated by reference in its entirety into this disclosure.

TECHNICAL FIELD

The present disclosure generally relates to metal ion separation, and in particular to a metal separation process using ligand-assisted chromatography.

BACKGROUND

This section introduces aspects that may help facilitate a better understanding of the disclosure. Accordingly, these statements are to be read in this light and are not to be understood as admissions about what is or is not prior art.

Metals in general, and in particular rare earth elements (REE's), are critical components of many high-valued products, such as petroleum refining catalysts, phosphors in color television and flat panel displays (cell phones, portable DVDs, and laptops), permanent magnets, and rechargeable batteries for hybrid and electric vehicles. Rare earth elements consists of 15 lanthanides (Ln's), scandium and yttrium. Currently, the REE's used in the U.S. are primarily imported from China, which produces more than 90% of the REE's used globally. Since China has reduced the export quota almost by half since 2010, it is highly desirable to develop efficient and cost-effective processes to produce and recover REE's domestically.

As an example, a typical production process for the rare earth elements can include the following steps: (1) physical separations (gravity concentration, flotation, magnetic, or electrostatic separation) which are used to separate rare earth minerals from sands and rocks in the ore; (2) dissolution of rare earth minerals in acidic or caustic solutions; (3) separation of each REE element from the mixture solutions; (4) precipitation of each REE element using oxalic acid to obtain solid REE oxalate, which is then decomposed under heat to form REE oxide of a single element. Among these steps, Step (3) is most challenging and costly because many of the REE's are present in the solution, and they have very similar chemical properties, ionic sizes, and charges.

The current large-scale production of REE's is mainly based on solvent extraction. Almost 20 sequential or parallel extraction steps using organic solvents (naphthenic acid or phosphorous-based extractants) and strong acids (hydrochoric acid or sulfuric acid) are needed to separate the REE's into eight or ten major fractions. Such a method requires large amounts of organic extractants and highly acidic or caustic aqueous solutions, which generates a lot of environmentally-hazardous wastes.

An alternative method to separate REE's is ligand-assisted displacement chromatography using an ion exchanger. In this method, the REE's are loaded onto a strong-acid cation exchange resin, and then displaced by sodium or ammonium ions in the presence of a ligand. In order to increase the purity and yield, a large column (0.45 L), a large amount of ligand solution (>130 column volumes), and a long displacement time (>3 weeks) are required to separate a small amount of REE's (<2 g), resulting in low productivity and poor ligand efficiency. Worse still, after each run, the column needs to be regenerated by a concentrated solution of acid or transition metal salt, which increases the operation cost significantly. As a result, this method is estimated to have a production cost of 40/kg, which is not economical for large-scale productions.

Another method to achieve REE's separation is extraction chromatography, in which a chelating agent is immobilized onto a resin to increase the selectivity of the sorbent for the REE's. The resins were developed by Argonne National Laboratory in the 1970's, and have been tested in analytical chromatography. Column test data showed that two small columns (with 0.3 g resin) can be used in tandem to capture and purify six REE's using two pH elution steps. However, the resin supply is limited at present, and the resin life is not well evaluated. Most importantly, the resin cost is over 16,000/kg, which is highly uneconomical for large-scale REE's separation.

There is therefore an unmet need for an efficient, cost effective method and system for achieving rare earth metal ion separation.

SUMMARY

In one aspect, a method for separating a mixture of ions, in particular, rare earth ions, is presented. The method comprises the steps of dissolving a mixture of metals in a strong acid to result in a dissolved mixture; capturing the desired metal ions in a first set of chromatography columns; washing the columns in a salt solution to remove non-adsorbing or weakly-adsorbing species; co-eluting the washed columns with a ligand solution to result in a further washed solution; and loading the further washed solution onto a second set of chromatography columns. The mixture of ions comprises metal ions. In another aspect, the metal ions comprise rare earth element ions. In yet another aspect, the metal ions comprise lanthanide ions. In yet another aspect, the metal ions comprise at least one lanthanide ion. In another aspect, the salt solution is a sodium salt solution. In another aspect, the salt solution is an ammonium salt solution.

In another aspect, the metal ions are absorbed in the second set of chromatography columns onto a solid phase, reacted with the ligand in a solution phase, and are eluted separately. The metal ions can be eluted separately by using the ligand solution with a linear gradient of ligand concentration. The metal ions can be eluted separately by using the ligand solution with a linear gradient of pH. The metal ions can also be eluted separately by using the ligand solution with stepwise changes in ligand concentration. The metal ions can also be eluted separately by using the ligand solution with stepwise changes in pH.

In yet another aspect, the metal ions are first dissolved in a 0.1 M-2 M strong acid solution. The strong acid can be one or a combination of hydrochloride acid (HCl), sulfuric acid ($H_2SO_4$), or nitric acid ($HNO_3$). The salt solution has a concentration of about 0.01 M to about 2 M. In another aspect, the salt solution comprises co-ions, including one of the following chloride ($Cl^-$), sulfate ($SO_4^{2-}$), bisulfate ($HSO_4^-$), and nitrate ($NO_3^-$). The first set of chromatography columns used to capture the desired metal ions can be packed with strong-acid cation exchange resins or other exchangers. The ligand used to elute the metal ions can form complexes with metal ions with different equilibrium constants (or stability constants). The ligand comprises, for example, ethylenediaminetetraacetic acid (EDTA), pentetic acid (DTPA), 1,2-Diaminocyclohexanetetraacetic acid (DCTA), N-(2-Hydroxyethyl) ethylenediamine-N,N',N'-triacetic acid (HEDTA), iminodiacetic acid (IDA), or citric acid. In one aspect, the ligand is EDTA.

In another aspect, the second set of chromatography columns used to separate the metal ions is packed with a robust adsorbent, which can have adsorption sites for the metal ions, or a ligand immobilized either covalently or via strong physical adsorption. In another aspect, the adsorbent is a ligand-preloaded adsorbent having a similar affinity but small or opposite selectivity for the metal ions compared to the ligand. In one embodiment, the adsorbent is a hydrous polyvalent metal oxide. In yet another aspect, the hydrous polyvalent metal oxide can be $TiO_2$. In yet another aspect, the hydrous polyvalent metal oxide can be $ZrO_2$. In yet another aspect, the hydrous polyvalent metal oxide can be $SnO_2$. In yet another aspect, the adsorbent comprises chelating resins with functional groups of iminodiacetic acid. In yet another aspect, the adsorbent comprises other ligands or adsorption sites.

In one aspect, the metal ions comprise at least one of praseodymium (Pr), neodymium (Nd), and samarium (Sm). In yet another aspect, the capture and separation of metal ions, specifically lanthanides, are carried out at a temperature in the range of about 0° C. to about 100° C. In another aspect, the capture and separation of lanthanides are carried out at a pressure between about 0.5 atmospheres and about 400 atmospheres. In yet another aspect, the temperature is in the range of 15° C. to 25° C., and the pressure is 1 atm. In yet another aspect, the separation is performed at a pH in the range of about 3 to about 11 and a ligand concentration between about 0.001 M and about 1 M. In yet another aspect, the separation is performed at pH 9 and the ligand concentration is in the range of 0.1 M to 0.4 M. In yet another aspect, the separation of metal ions is performed in at least one of a batch mode with a linear gradient elution, a batch mode with a stepwise gradient elution, or a continuous mode with a stepwise gradient elution.

DETAILED DESCRIPTION

Figure 1:
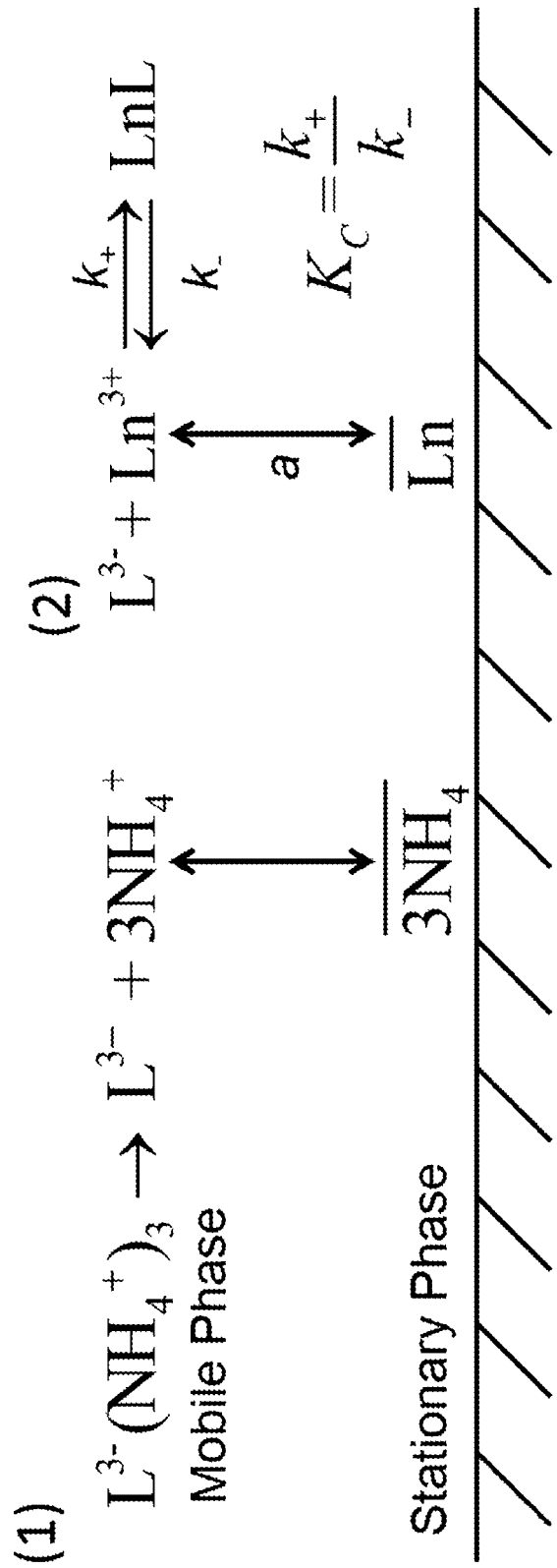
FIG. 1 is an illustration depicting the adsorption and complexation mechanisms of lanthanides (Ln's) in the ligand-assisted elution chromaography.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended. In addition, it should be appreciated that although the separation of lanthanides is presented in this disclosure, this is only for demonstrative purposes and is not intended to be limiting of the scope of this disclosure, and the processes described herein can thus be applied to metal ions, including but not limited to rare earth element ions. Rare earth element ions can include cerium, dysprosium, erbium, europium, gadolinium, holmium, lanthanum, lutetium, neodymium, praseodymium, promethium, samarium, scandium, terbium, thulium, ytterbium, and yttrium.

Presented herein is a novel ligand-assisted elution chromatography process for the separation of metal ions, rare earth element ions, and lanthanides (Ln's) using a robust and low-cost sorbent. The sorbent can be organic or inorganic. In one embodiment, the inorganic sorbent is titania. The adsorbent is a ligand-preloaded adsorbent having a similar affinity but small or opposite selectivity for the metal ions compared to the ligand. In an embodiment, the titania column is first preloaded with a ligand solution. The separation of Ln's is used as an example here. After the Ln's mixture is loaded onto the ligand-immobilized column, the ligand solution is used to elute the adsorbed Ln's. The element that can form a more stable complex with the ligand elutes earlier in the effluent. Analysis showed that the overall selectivity equals the ratio of the ligand selectivity to the sorbent selectivity. In addition, the Ln's can be well separated only if the adsorption isotherm parameters and complexation equilibrium constants are in the same order of magnitude.

Based on the results, several ligands were screened, among which ethylenediaminetetraacetic acid (EDTA) was found to have the best complexation equilibrium constants for separating the Ln's on a titania column. A ternary separation of Pr, Nd, and Sm was tested using EDTA. Pure products of each element were obtained with high purity under well-designed ligand concentrations. Linear-gradient elution was used to concentrate the products and shorten the cycle time. The recovery yields for high-purity Ln's (>95%) exceed 95% for all three products. Rate model simulations taking into account adsorption, mass transfer, and reactions were developed to verify the mechanism of ligand-assisted elution and separation. The simulation results agree closely with the experimental data.

The separation process disclosed herein is much more efficient than the conventional sequential and parallel solvent extraction processes. All the REE's can be separated within one set of chromatography columns under room temperature and relatively mild pH conditions. Both the sorbent and the ligand are inexpensive and readily available. The ligand is generally recognized as safe and most of the ligand can be recycled after each run. No harsh or expensive chemicals are needed for column regeneration. To increase sorbent productivity and to reduce the amount of ligand required and the production cost, a continuous countercurrent chromatography process with step-wise elution can be used for large-scale production.

The separation of metal ions in a ligand-assisted chromatography system is controlled by both adsorption and complexation reactions in the mobile phase (FIG. 1). FIG. 1 illustrates the adsorption and complexation of Ln's in the ligand-assisted elution chromaography. Still referring to FIG. 1, L is the ligand, Ln is the lanthanide, LLn is the complex formed by the ligand and the lanthanide. $K_C$ is the complexation equilibrium constant, a is the linear Langmuir isotherm parameter. The sorbent is presaturated with the ligand, which adsorbs on the sorbent. The adsorbed ligand is a part of the stationary phase, and not shown explicitly in FIG. 1. The counter-ion of the ligand $NH_4^+$ can compete with Ln's for the Brønsted acid site and the ligand-preloaded Lewis acid site in titania. $NH_4^+$, which is the co-ion of the ligand, may weakly adsorb onto the adsorbent and thus affect the retention of Ln peaks. The mechanism of Ln adsorption onto the ligand-immobilized titania is explained further below, and in addition, the key controlling factors on Ln's elution and separation in ligand-assisted chromatography are described. The rate model and simulations are described as well.

Figure 2A:
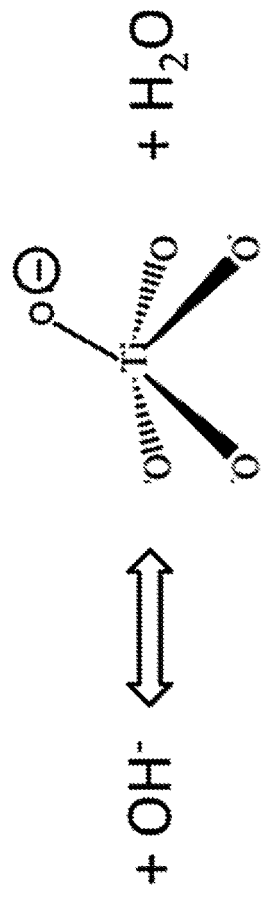
FIG. 2a shows the properties of Brønsted acid sites on the titania adsorbent.
Figure 2A:
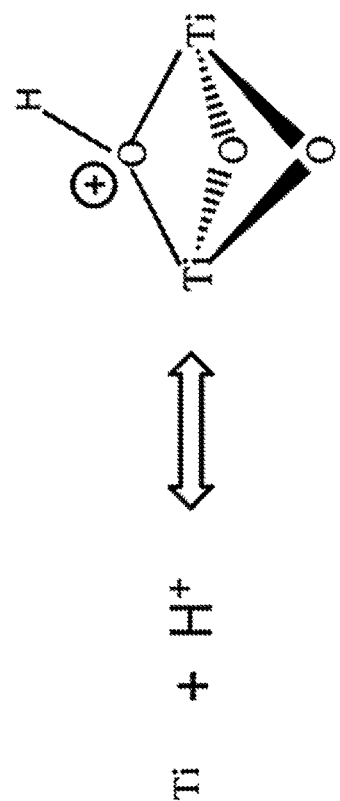
Figure 2A:
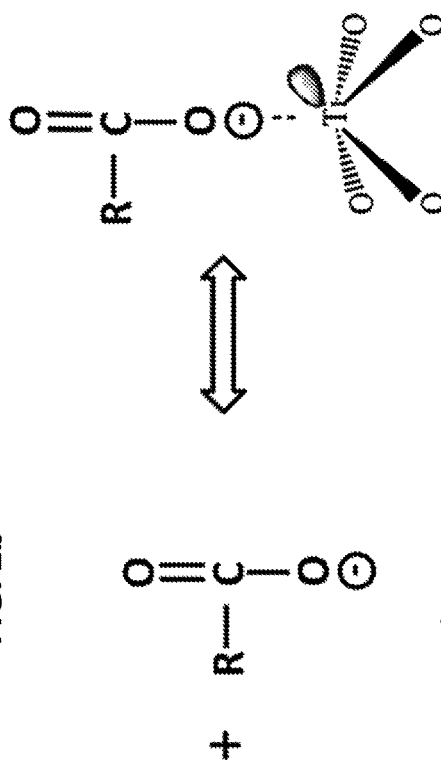
Figure 2A:
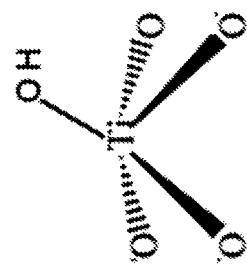
Figure 2B:
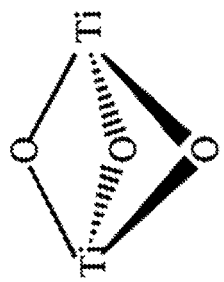
FIG. 2b shows the properties of Brønsted base sites on the titania adsorbent.
Figure 2C:
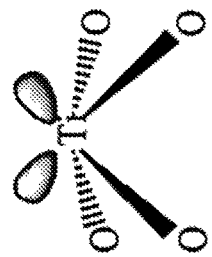
FIG. 2c shows the properties of Lewis acid sites, on the titania adsorbent.

Adsorption Mechanism:

Titania is a complex sorbent with three types of adsorption sites (FIGS. 2a-2c): Brønsted acid (BA), Brønsted base (BB), and Lewis acid (LA) sites. FIG. 2a shows the properties of Brønsted acid sites, FIG. 2b shows the properties of Brønsted base sites, and FIG. 2c shows the properties of Lewis acid sites, on the titania adsorbent. At a high pH, the protons on the BA sites (TiOH) can react with the $OH^-$ in the solution, and the resulting $TiO^-$ groups have a high affinity for cations (FIG. 2a). At a low pH, the protons in the solution can adsorb on the BB sites (Ti—O—Ti), which in turn can bind anions (FIG. 2b). The LA sites (Ti) are coordinatively unsaturated titanium atoms, which have vacant orbitals for electrons (FIG. 2c). Many Lewis bases with extra electrons, such as $OH^-$, $PO_4^{3-}$, $SO_4^{2-}$, and $COO^-$, can adsorb strongly onto the LA sites. If the adsorbed Lewis bases have more charges than needed for adsorption, they can serve as additional adsorption sites for cations.

If a ligand with multiple $COO^-$ groups is preloaded onto a titania sorbent, some of the $COO^-$ groups can bind strongly with the LA sites. Under this condition, the Ln's can adsorb on both the BA sites and the free $COO^-$ groups of the ligand adsorbed on the LA sites. The adsorption data can be correlated using a Bi-Langmuir isotherm model according to Eq. (1):

$$q = \frac{a_1 C}{1+b_1 C} + \frac{a_2 C}{1+b_2 C} \quad (1)$$

where q and C are the solid-phase and the liquid-phase concentrations in local equilibrium; a and b are the linear and nonlinear Langmuir isotherm parameters; subscripts "1" and "2" represent Sites 1 (BA sites) and Sites 2 (LA sites), respectively.

However, if a ligand is present in the mobile phase, the adsorption sites which have much weaker affinity for the Ln's than the ligand will not be able to retain Ln's. Retention is needed to allow the complexation reactions in the mobile phase to accelerate the migration of the Ln's that have higher affinity for the ligand. The effects of adsorption and complexation on Ln separation are discussed below.

Ligand-Assisted Elution Chromatography:

In conventional elution chromatography, the migration of solutes along the column results from repetitive adsorption and desorption. In ligand-assisted elution chromatography, the adsorption is strong, and the desorption is driven by a reversible complexation of Ln or metal ions and the ligand in the liquid phase (FIG. 1). Since different metal ions can form complexes with the ligand with different complexation equilibrium constants, they can migrate at different velocities in the column, resulting in the separation.

For a linear isotherm system, the retention factor of a solute peak in the presence of a ligand has the following expression according to Eq. (2):

$$k' = \frac{1}{\varepsilon_t} \frac{a}{1+K_C[L]} \quad (2)$$

where $\varepsilon_t$ is the total void fraction in the column, $K_C$ is the complexation equilibrium constant, and $[L]$ is the ligand concentration. The product $K_C[L]$ can be considered as a dimensionless complexation equilibrium constant. It is noteworthy that "a" must be in the same order of magnitude as $K_C[L]$ to guarantee a reasonable time scale for elution. If $a \ll K_C[L]$, the complexation reaction is much stronger than the adsorption, resulting in elution of the solutes at the void volume. If $a \gg K_C[L]$, the complexation is too weak compared to the adsorption; the solute is likely to be trapped in the column and cannot be eluted.

The ratio of the retention factors of two solutes gives the overall selectivity in the system, as shown in Eq. (3).

$$\alpha = \frac{k_2'}{k_1'} = \left(\frac{a_2}{a_1}\right)\left(\frac{1+K_{C1}[L]}{1+K_{C2}[L]}\right) \quad (3)$$

In most cases, the complexation is strong and $K_C[L] \gg 1$, so that Eq. (3) can be reduced to Eq. (4).

$$\alpha = \left(\frac{a_2}{a_1}\right)\left(\frac{K_{C1}}{K_{C2}}\right) = \frac{\alpha_{Adsorbent}}{\alpha_{Ligand}} \quad (4)$$

where $\alpha_{Sorbent}=a_2/a_1$ is the sorbent selectivity, and $\alpha_{Ligand}=K_{C2}/K_{C1}$ is the ligand selectivity. If the sorbent has little selectivity for the solutes, the overall selectivity is dominated by the ligand selectivity.

For a nonlinear isotherm system, the retention factor does not have a simple analytical expression. In addition, the co-ion of the ligand, $NH_4+$, can also adsorb weakly onto the ligand-loaded LA sites and affect the retention of Ln peaks. Nevertheless, the results obtained from the linear isotherm system can still serve as the guidelines for designing non-linear isotherm systems. To achieve efficient and high-purity separation, one has to select the ligand such that $K_C[L]$ has the same order of magnitude as a, and the ratio $\alpha_{Ligand}/\alpha_{Sorbent}$ should be 1.2 or larger.

VErsatile Reaction and SEparation (VERSE) model and simulation:

The VERSE model and simulations take into account multiple mass-transfer effects (axial dispersion, film mass transfer, intra-particle pore and surface diffusion) in chromatography, and incorporates a variety of models for adsorption (including Langmuir, Bi-Langmuir, Freundlich, and Mass action) and reactions (aggregation, decomposition, isomerization, etc.). A simulation program can numerically solve the partial differential mass balance equations in the bulk phase and the particle phase. The effluent histories and dynamic column profiles can be displayed and exported after the simulations are completed. The figures and animations generated by the simulations are important for verifying the models and the separation mechanisms.

In simulating the Ln separation processes, we used the pore diffusion model, the assumptions and equations of which have been reported elsewhere. The axial dispersion coefficient was estimated from Chung and Wen correlation, and the film mass-transfer coefficient was obtained from the Wilson and Geankoplis correlation. Although the titania has two types of sites (BA and LA) for Ln adsorption, the BA sites were found to have much weaker affinity for the Ln's than the ligand, and thus have negligible effect on the retention of Ln peaks. Therefore, we considered only the high-affinity sites, or the ligand-loaded LA sites, in the simulations, and used the Langmuir adsorption isotherm model instead of the Bi-Langmuir model.

The actual values of $K_C$, a, and b are large ($>10^7$). If they are used in the simulations, the time required for convergence would be extremely long. In fact, as long as $K_C[L]$ is much greater than 1, the retention of peaks depends primarily on a dimensionless ratio $a/K_C[L]$, Eq. (2), rather than the individual values of a, b, and $K_C$. It has been verified in the simulations that when the value of $a/K_C[L]$ is fixed, increasing both a and $K_C[L]$ does not affect the peak shape or retention time. In order to simulate the separation processes more efficiently without affecting the peak retention, we scaled down the values of a, b, and $K_C$, while satisfying the following: (1) The ratio $K_C(Sm):K_C(Nd):K_C(Pr)$ is the same as that reported by the literature; (2) The ratio a(Sm):a(Nd):a(Pr) is the same as the experimental data; (3) The adsorption capacity, or the value of a/b, is consistent with the experimental data; (4) The values of $K_C[L]$ are much greater than 1, and they are similar to the Langmuir a values.

Materials and Methods:

The materials and experiments described below were used to separate the Ln's and to understand the mechanisms of Ln's separation. Solution preparation, pH measurement, column packing, and column tests were all performed at room temperature, 20±1° C.

Materials:

Praseodymium (III) nitrate hexahydrate ($Pr(NO_3)_3 \cdot 6H_2O$), neodymium (III) nitrate hexahydrate ($Nd(NO_3)_3 \cdot 6H_2O$), and samarium (III) nitrate hexahydrate ($Sm(NO_3)_3 \cdot 6H_2O$) were ordered from Sigma-Aldrich, Co. (St. Louis, Mo.). The ligands ethylenediaminetetraacetic acid (EDTA) and diethylenetriaminepentaacetic acid (DTPA) were also purchased from Sigma-Aldrich, Co. (St. Louis, Mo.), whereas citric acid was purchased from J. T. Baker (Phillipburg, N.J.). The sorbent Sachtopore 80 ($TiO_2$, 80 μm, 60 Å) was manufactured by ZirChrom Separations, Inc. (Anoka, Minn.). Sodium hydroxide (NaOH), nitric acid ($HNO_3$), and ammonium hydroxide ($NH_4OH$) were purchased from Mallinckrodt Baker, Inc. (Paris, Ky.). Distilled Deionized Water (DDW) was obtained from a Millipore (Bedford, Mass.) four stage cartridge system.

Millipore glass columns (60 cm L×1.1 cm ID) and Omnifit glass columns (15 cm L×1.5 cm ID) were ordered from VWR International (West Chester, Pa.) for sorbent packing. An AKTA explorer 100 unit (GE Healthcare, Piscataway, N.J.), which consists of a P-901 binary pump, an M-925 mixer, a UV-900 UV-absorption monitor (able to simultaneously monitor at three wavelengths), a pH/C-900 online pH, a conductance monitor, and a Frac-950 fraction collector, was used for chromatography experiments. A Dell-PC with Unicorn 5.01 software was connected to the AKTA unit for data storage and processing.

Displacement Test:

The displacement test was used to check if the sorbent Sachtopore 80 (S80) has sufficiently high selectivity to separate the Ln's. The column size was 49 cm L×1.16 cm ID. After the column was packed, it was washed with 0.2 M NaOH, 0.2 M $HNO_3$, and DDW, to remove any impurities in the sorbent. A 30 mL solution of Pr, Nd and Sm (0.02 N for each element) was then fed into the column. After the feed loading, a solution of 0.05 M $HNO_3$ was pumped into the column to displace the adsorbed Ln's. The linear velocities for loading and displacement were both 0.2 cm/min Pr, Nd, and Sm were detected using an online UV-vis detector at 444 nm, 575 nm, and 401 nm, respectively. $HNO_3$ was monitored using an online pH sensor. After the bands of Pr, Nd, and Sm were displaced by the $HNO_3$ front, the displacement was stopped and the column was washed with DDW for 50-100 column volumes until the pH returned to 6 and the conductivity dropped below 0.003 mS/cm.

Ligand-Assisted Elution Tests:

In ligand-assisted elution tests, the S80 column (49 cm L×1.16 cm ID) was first preloaded with a ligand solution, the pH of which was adjusted to a target value by titrating with $NH_4OH$. The Ln's (Pr, Nd, and Sm) were dissolved in the same ligand solution, and the concentrations were 0.02 N for each element. The column was then fed with 30 mL of the Ln solution, and subsequently eluted by the ligand solution. The linear velocities for loading and elution were both 0.2 cm/min Pr, Nd, and Sm were detected at 444 nm, 575 nm, and 404 nm, respectively.

DTPA (pH 9), EDTA (pH 9), and citric acid (pH 7) were tested for isocratic elution, whereas EDTA (pH 9) was also tested for linear gradient elution. In isocratic elution tests, the eluant was the same as the ligand solution used for preloading. In gradient elution, the ratio of the two pumps was programmed as a function of time, so that the ligand concentration could increase linearly from the preloading concentration to a target value. The experimental conditions for each ligand tested are summarized in Table 1. Before switching to a different ligand system, the column was washed with 0.2 M NaOH, 0.2 M HNO$_3$, and then DDW, until the pH returned to 6 and the conductivity dropped below 0.003 mS/cm.

TABLE 1

Experimental conditions for ligand-assisted elution tests

| Column size (cm L × cm ID) | Superficial velocity (cm/min) | Feed concentration (N) | Feed volume (mL) |
|---|---|---|---|
| 49 × 1.16 | 0.2 | 0.02 for Pr, Nd, Sm | 30 |

Isocratic elution

| Ligand | pH | Presaturant and Eluant Concentration (M) |
|---|---|---|
| DTPA | 9 | 0.04 |
| EDTA | 9 | 0.1, 0.2, 0.35, 0.4 |
| Citric acid | 7 | 0.2 |

Linear gradient elution

| Ligand | pH | Concentration (M) |
|---|---|---|
| EDTA | 9 | 0.1-0.4 |

Frontal Tests for Isotherm Estimation:

The adsorption isotherms for the Ln's were obtained by multiple frontal tests using a small S80 column (4.8 cm L×1.5 cm ID), which was washed in sequence with 0.2 M NaOH, 0.2 M HNO$_3$, and DDW prior to the tests. The isotherm measurement was first conducted in the absence of ligand. The solutions prepared for the isotherm measurement were 0.002 N, 0.005 N, 0.01 N, 0.02 N, 0.05 N, and 0.1 N of Pr, Nd, and Sm in DDW. A more concentrated solution was loaded to the column once the sorbent was equilibrated with a less concentrated solution. After all the concentrations were tested for one Ln, the column was washed with 0.2 M HNO$_3$ and DDW, and then used for a different Ln. The Ln concentration in the sorbent, which is in equilibrium with a solution phase concentration, can be calculated as follows:

$$q_{i+1} = q_i + \frac{(C_{i+1} - C_i)V_{br,i+1}}{V_C} \quad (5)$$

where $C_i$ and $C_{i+1}$ are the solution phase concentrations at the $i^{th}$ and $(i+1)^{th}$ frontals; $q_i$ and $q_{i+1}$ are the sorbent phase concentration in equilibrium with $C_i$ and $C_{i+1}$, respectively. When i=0, $C_i$ and $q_i$ are both zero. $V_{br,i+1}$ is the net breakthrough volume (dead volume and void volume were subtracted) for the $(i+1)^{th}$ frontal; $V_C$ is the column packing volume.

The measurement of Ln adsorption isotherm on the ligand-immobilized sorbent was conducted on the same column (4.8 cm L×1.5 cm ID), which was preloaded with 0.4 M EDTA (pH 9). Before the Ln's were loaded, the system was washed by 1 column volume ($V_C$) of DDW to avoid complexation of Ln's and EDTA in the tubing. The solutions prepared for the isotherm measurement were 0.001N, 0.002 N, 0.005 N, 0.01 N, 0.02 N, 0.05 N, and 0.1 N of Pr, Nd, and Sm in DDW. Unlike the ligand-free isotherm tests, the column was regenerated by the 0.4 M EDTA solution and washed by 1 $V_C$ of DDW each time before it was loaded with a different concentration or a different element. As a result, the sorbent phase Ln concentration can be simply calculated using Eq. (6).

Figure 3:
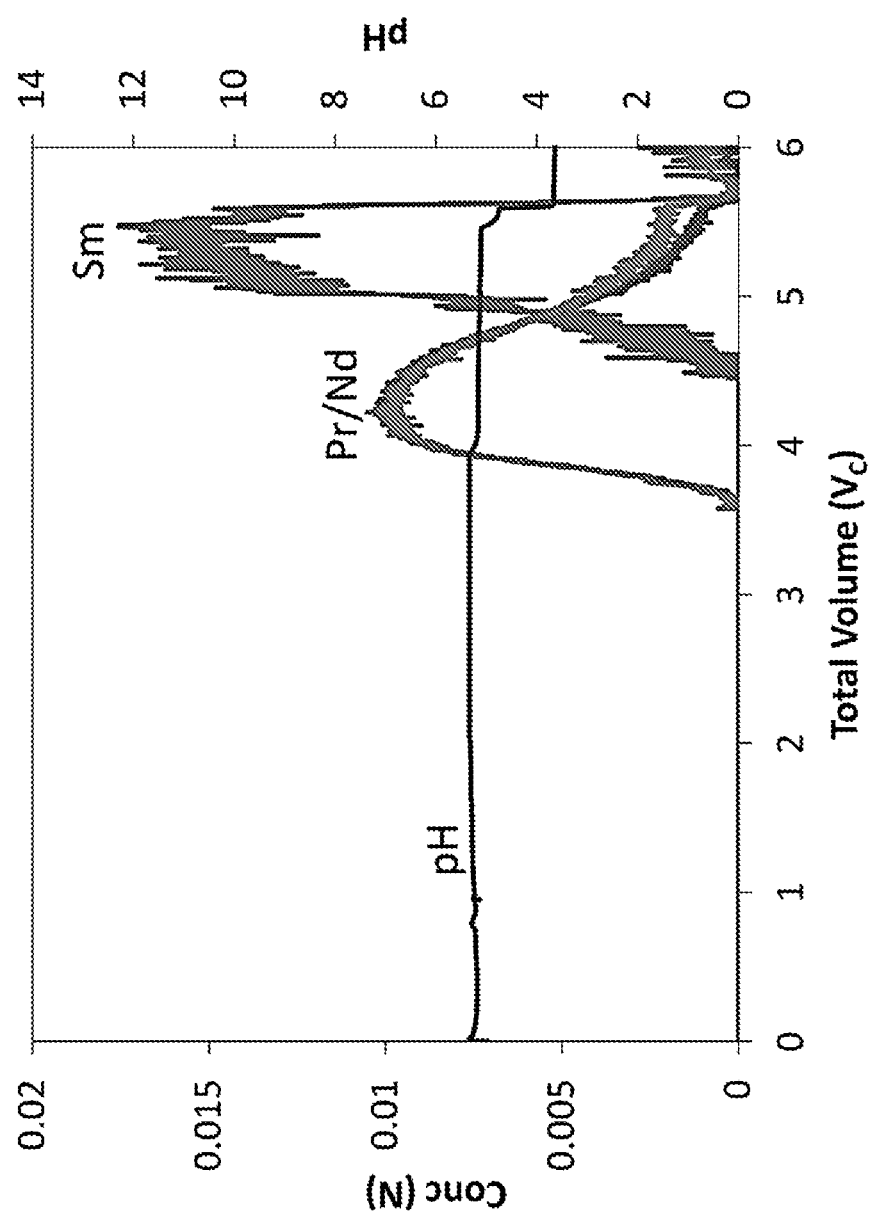
FIG. 3 shows effluent history of Pr, Nd, and Sm in a displacement test using titania.

Results:

Elution Behaviors of Ln's in the Displacement Test:

In the displacement test, the adsorbed Pr, Nd, and Sm were displaced from the titania sorbent by 0.05 M HNO$_3$. The chromatogram is shown in FIG. 3 (specifically, FIG. 3 shows the effluent history of Pr, Nd, and Sm in the displacement test using titania; the column size is 49 cm L×1.16 cm ID; the superficial velocities for loading and displacement are both 0.2 cm/min; the feed concentration is 0.02 N for each element, and the feed volume is 30 mL; the pH sensor reading is inaccurate due to device limitations, it is able to show the breakthrough of HNO$_3$ behind the Sm band). The total volume shown in FIGS. 3-7 includes extra-column dead volume (0.13 $V_C$), total void volume (0.62 $V_C$), and feed loading volume (0.58 $V_C$). The pH values monitored by the online sensor were inaccurate due to device limitations, but the changes in pH indicate the breakthrough time of HNO$_3$ front. The bands of Pr and Nd overlapped, indicating that the sorbent has no selectivity for these two elements. The sorbent has higher affinity for Sm than for Pr and Nd, so the band of Sm was behind those of Pr and Nd. However, the bands of Pr and Nd had significant tailing and the band of Sm was thus contaminated. As a result, the selectivity of titania sorbent was found insufficient to achieve high-yield and high-purity separation for the Ln's.

Figure 4A:
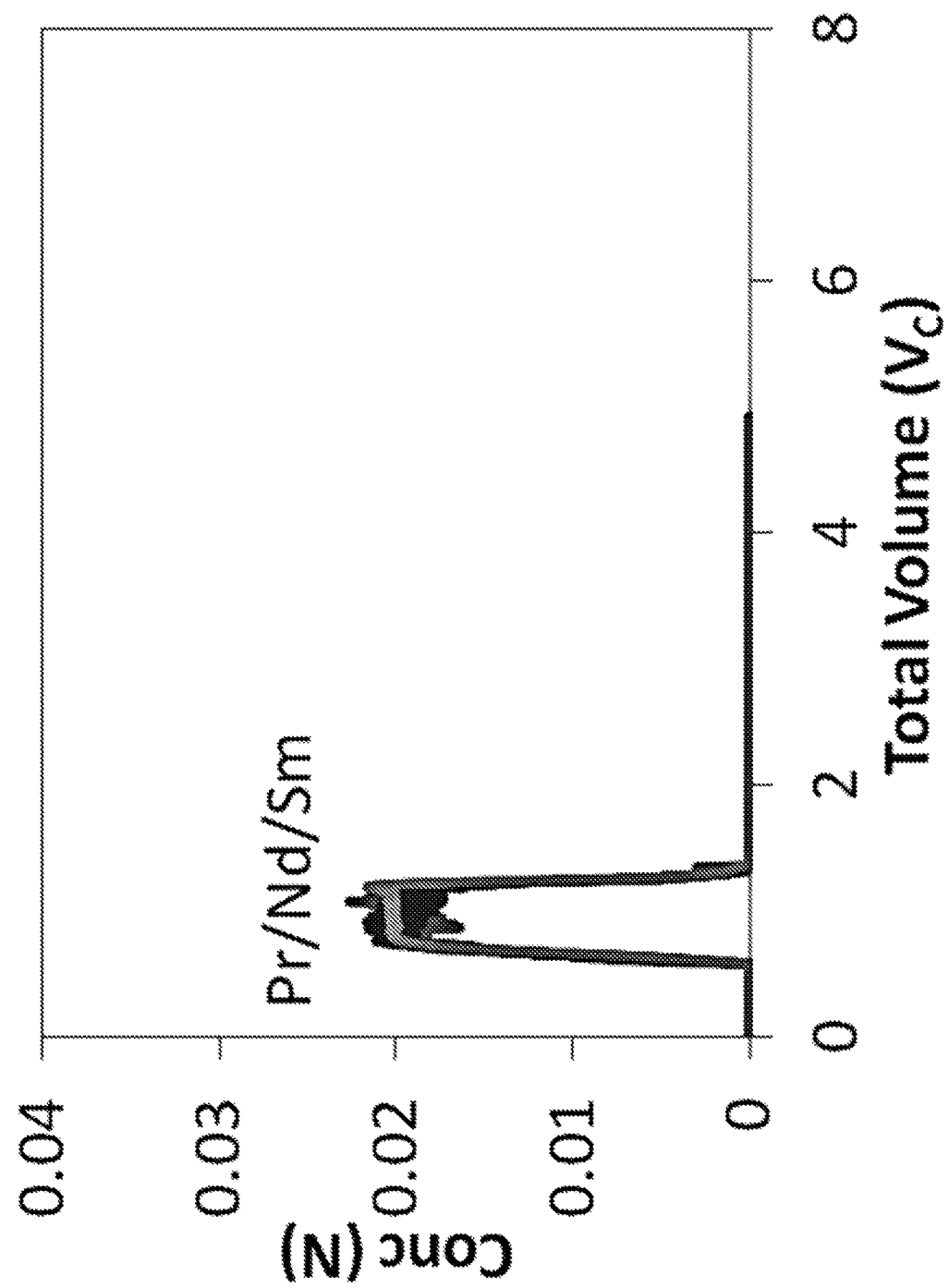
FIG. 4a shows the effluent history of Pr, Nd, and Sm for the ligand-assisted elution using 0.04 M DTPA.
Figure 4B:
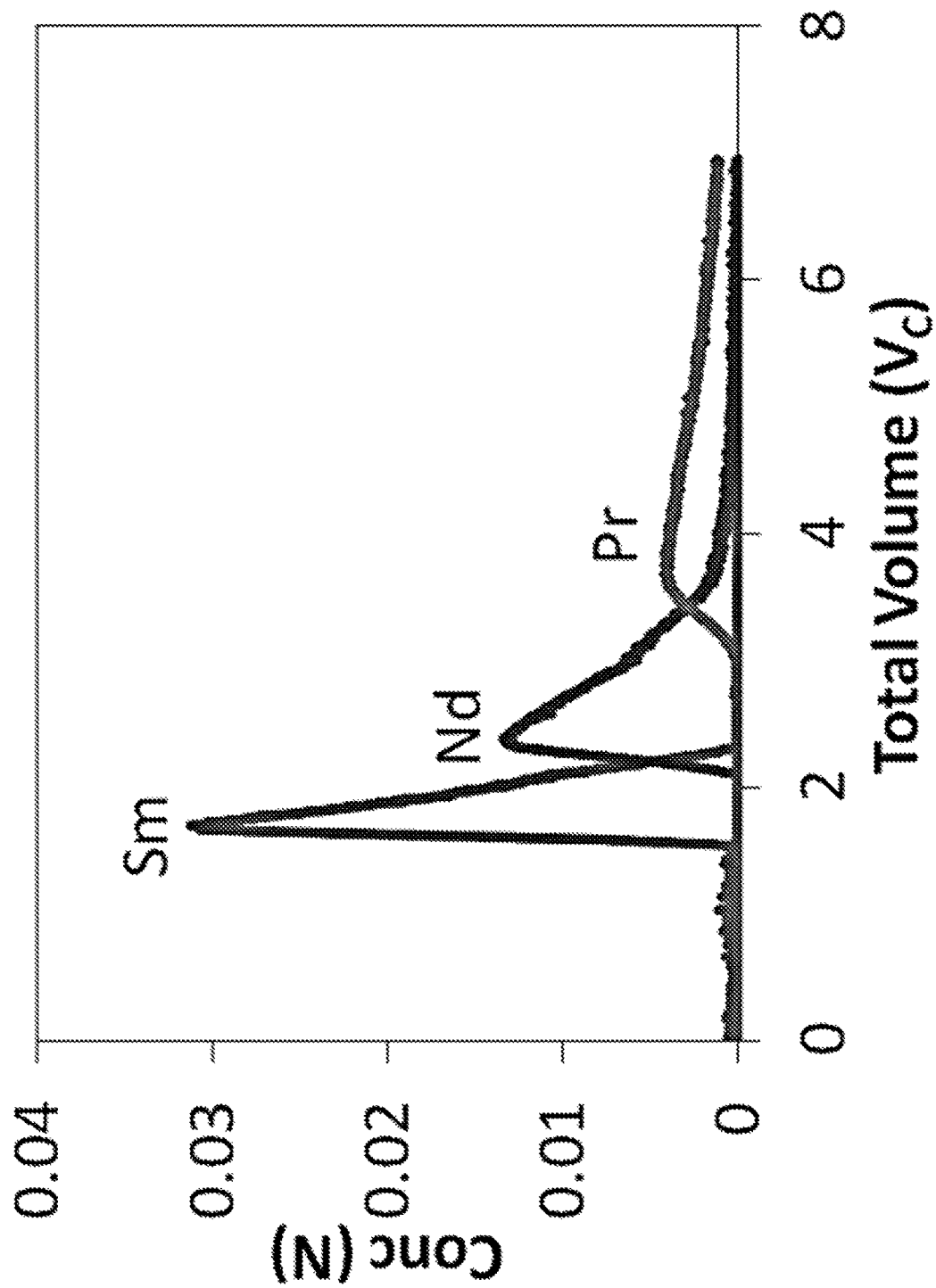
FIG. 4b shows the effluent history of Pr, Nd, and Sm for the ligand-assisted elution using 0.2 M EDTA.

Comparison of Various Ligands in the Elution Tests:

As shown in Table 1, three ligand candidates, DTPA, EDTA, and citric acid, were screened via the elution tests, the procedure of which were described above. The chromatograms obtained from the elution tests using DTPA and EDTA are shown in FIGS. 4a and 4b, respectively. FIGS. 4a and 4b show the effluent history of Pr, Nd, and Sm for the ligand-assisted elution using 0.04 M DTPA (FIGS. 4a) and 0.2 M EDTA (FIG. 4b). The experimental conditions are shown in Table 1.

When DTPA was used as the ligand, all the Ln's were co-eluted at the void volume. The reason is that DTPA complexes too strongly with the Ln's, which cannot adsorb onto the sorbent ($K_C[L]\gg a$). When EDTA was used, the Ln's were eluted separately with a reasonably small retention volume, because EDTA has a high selectivity for the Ln's, and the $K_C[L]$ for the complexation reaction has a similar value as the Langmuir a value for Ln's adsorption ($K_C[L]\sim a$). When citric acid was used, none of the Ln's were eluted after 10 column volumes (not shown in FIGS. 4a and 4b). The complexation was apparently too weak compared to the Ln's adsorption ($K_C[L]\ll a$), and the Ln's thus strongly adsorbed on the column. To avoid the accumulation of Ln's in the column, concentrated EDTA solution (0.4 M, pH 9) was used as the eluant, and all the Ln's were completely eluted as a single band at the void volume.

Figure 5A:
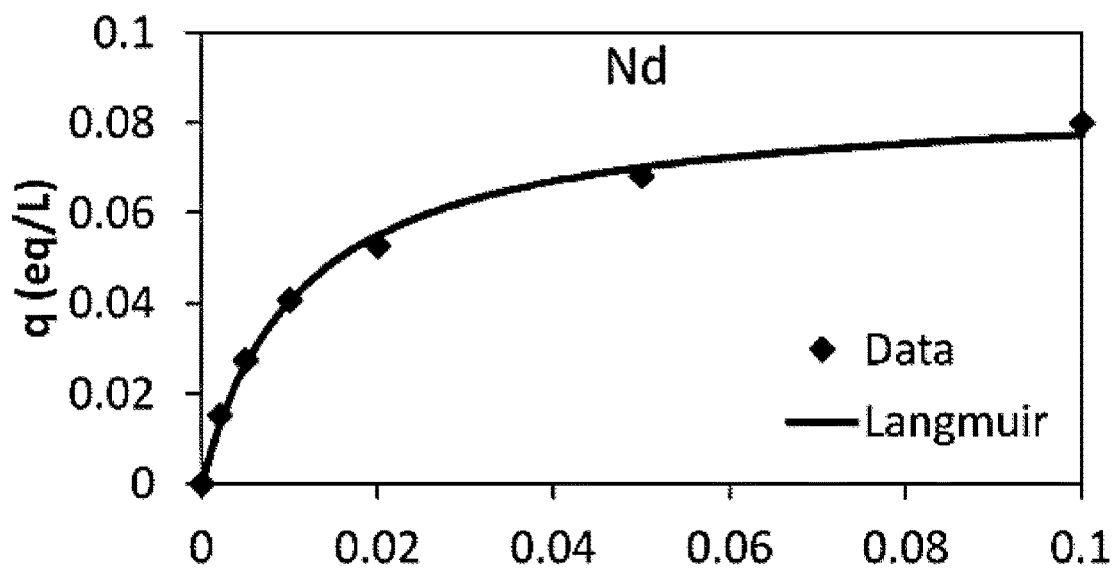
FIG. 5a shows the adsorption isotherms of Nd on EDTA-free titania adsorbent.
Figure 5B:
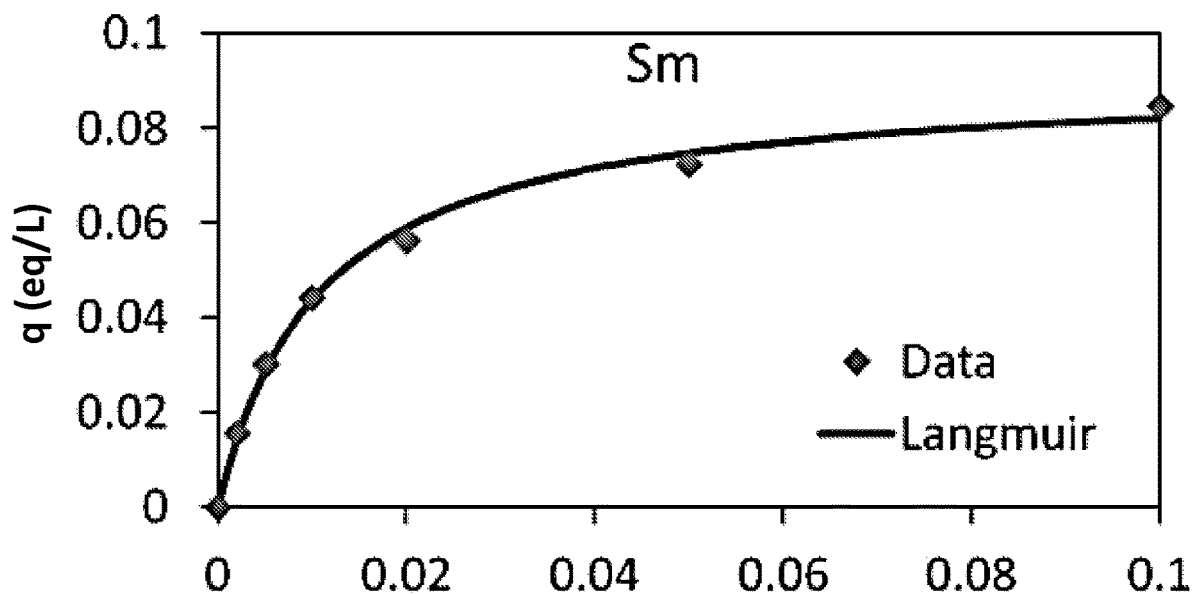
FIG. 5b shows the adsorption isotherms of Sm on EDTA-free titania adsorbent.

Ln's Adsorption Isotherms on the Titania Sorbent:

In the absence of a ligand, the Ln's, if dissolved in DDW, can adsorb weakly on the BA sites of the titania. The pH values of the Ln solutions were around 5. The adsorption isotherms of Nd and Sm on EDTA-free titania adsorbent are shown in FIGS. 5a and 5b, respectively. The isotherm of Pr was found to be identical to that of Nd, and was not shown separately. The experimental data were correlated closely using the Langmuir isotherm model, and the parameters obtained from the data are listed in Table 2.

TABLE 2

Langmuir and Bi-Langmuir isotherm parameters

| Sorbent | Model | Isotherm parameters | Pr/Nd | Sm |
|---|---|---|---|---|
| EDTA-free titania | Langmuir | a | 7.6 | 8.4 |
| | | b (1/N) | 88.3 | 92.4 |
| | | $R^2$ | 0.995 | 0.995 |
| EDTA-preloaded titania | Langmuir | a | 44.8 | 47.9 |
| | | b (1/N) | 128.1 | 140.9 |
| | | $R^2$ | 0.920 | 0.866 |
| | Bi-Langmuir | $a_1$ | 14.7 | 10.3 |
| | | $b_1$ (1/N) | 44.7 | 31.1 |
| | | $a_2$ | $1.2 \times 10^7$ | $2.3 \times 10^7$ |
| | | $b_2$ (1/N) | $1.6 \times 10^8$ | $2.4 \times 10^8$ |
| | | $R^2$ | 0.976 | 0.980 |

Figure 5C:
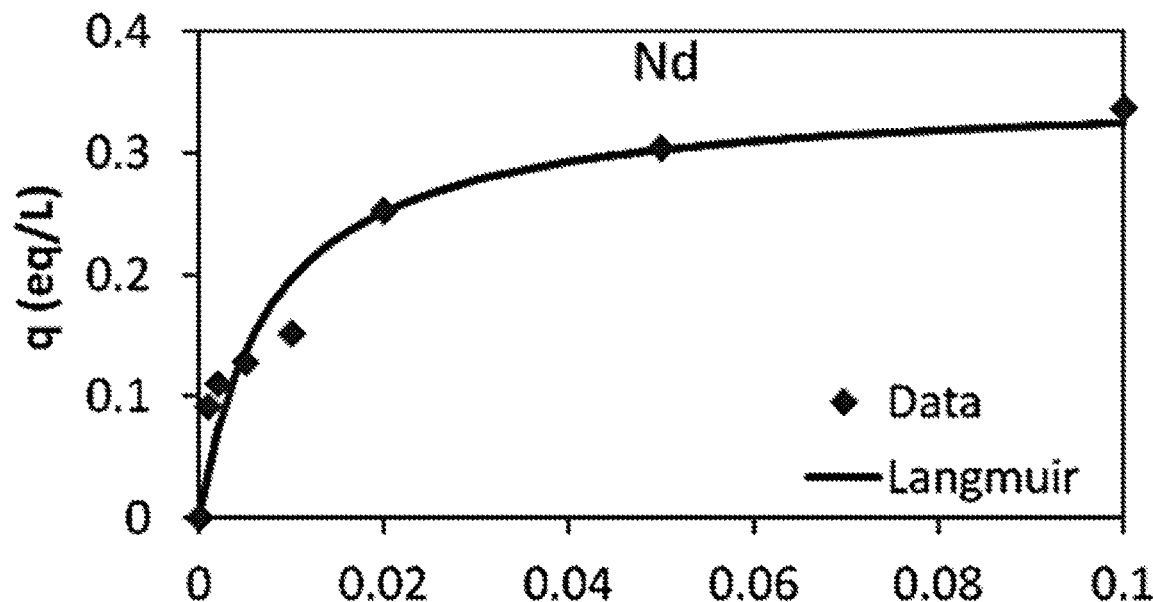
FIG. 5c shows the adsorption isotherms for Nd EDTA-preloaded titania adsorbent.
Figure 5D:
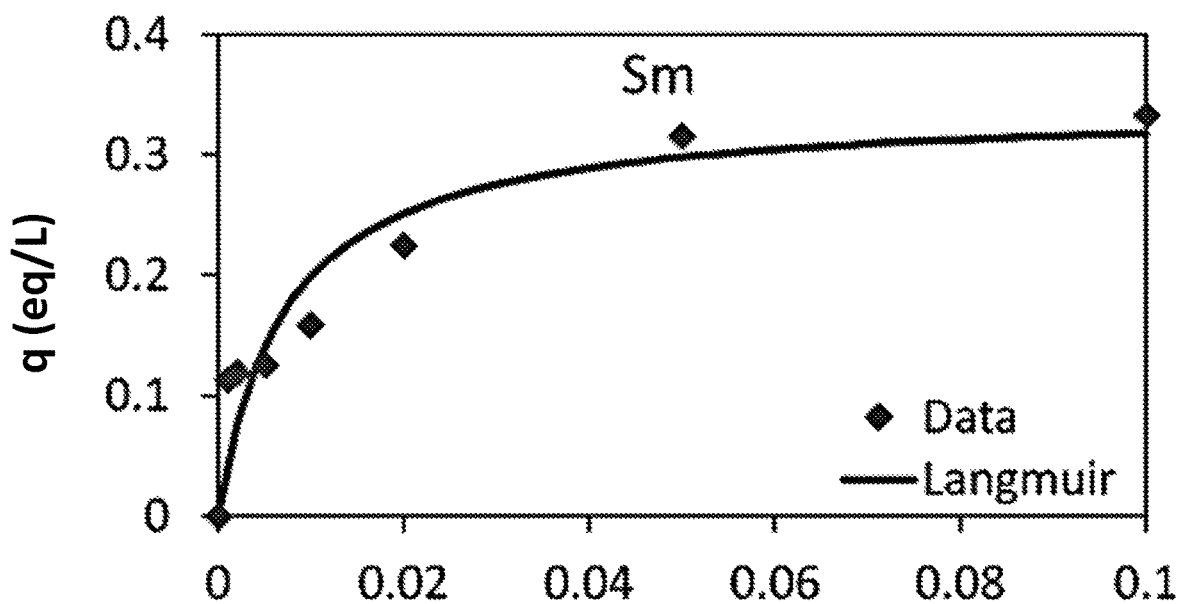
FIG. 5d shows the adsorption isotherms for Sm on EDTA-preloaded titania adsorbent.
Figure 5E:
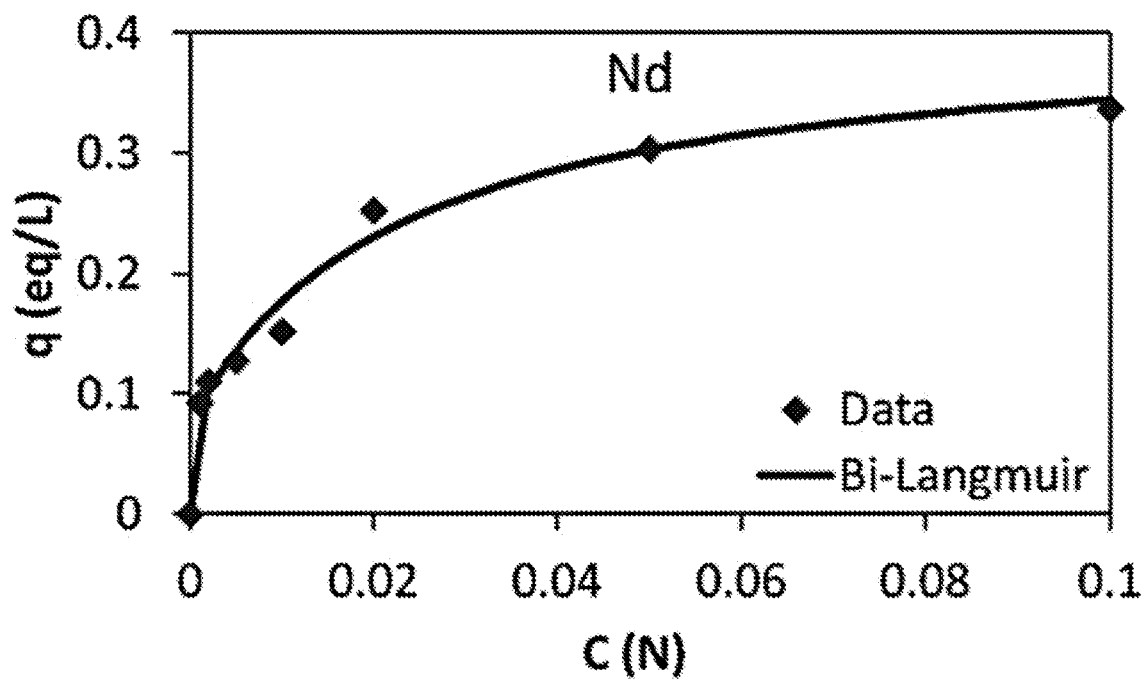
FIG. 5e shows the Bi-Langmuir model as tested for Nd.
Figure 5F:
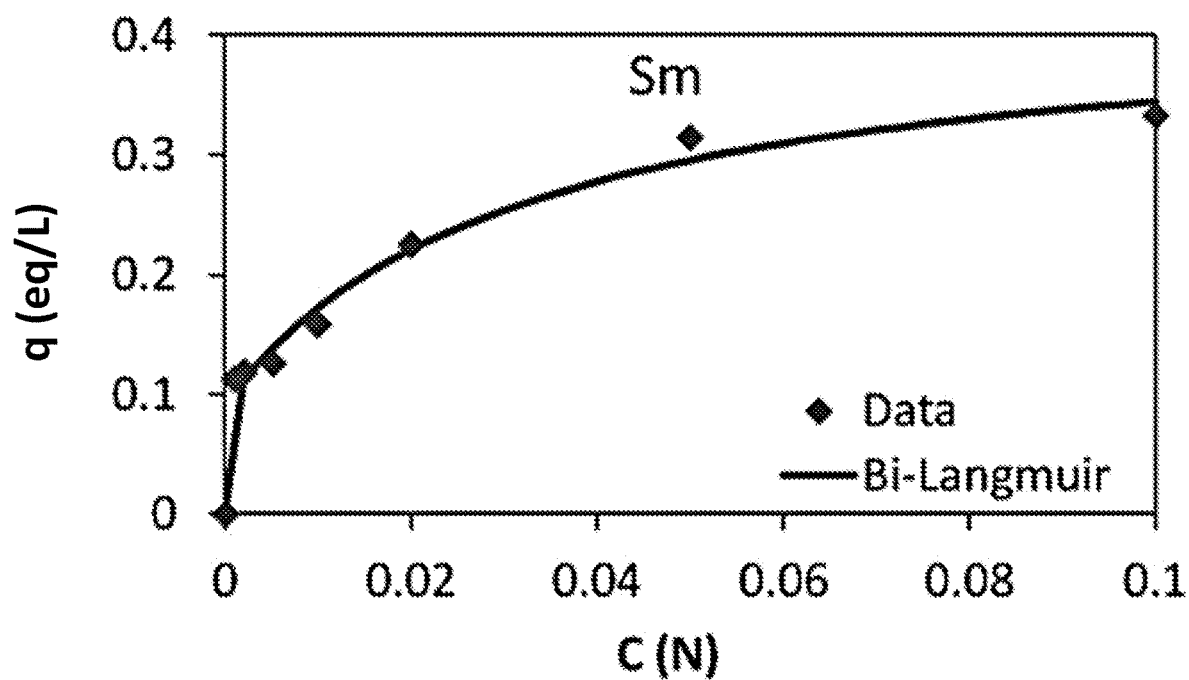
FIG. 5f shows the Bi-Langmuir model as tested for Sm.
Figure 6B:
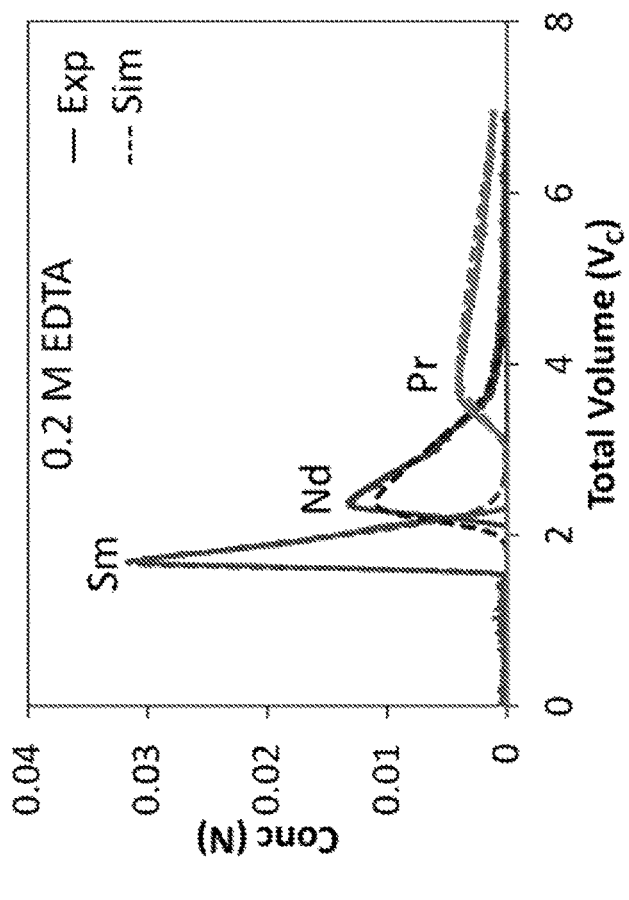
FIG. 6b shows results from isocratic elution tests at the EDTA concentration of 0.2 M for the separation of Pr, Nd, and Sm using EDTA (pH 9) as the ligand.
Figure 6A:
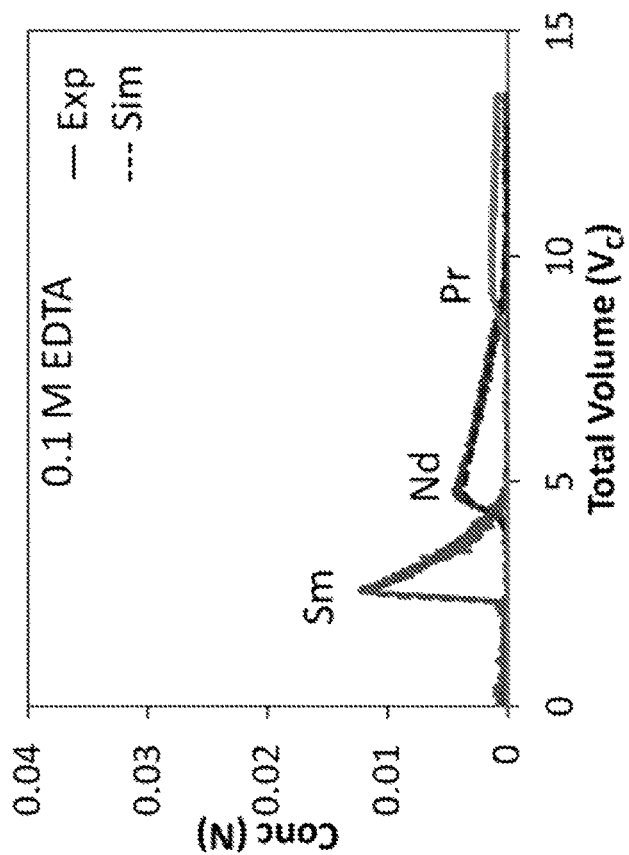
FIG. 6a shows results from isocratic elution tests at the EDTA concentration of 0.1 M for the separation of Pr, Nd, and Sm using EDTA (pH 9) as the ligand.
Figure 6D:
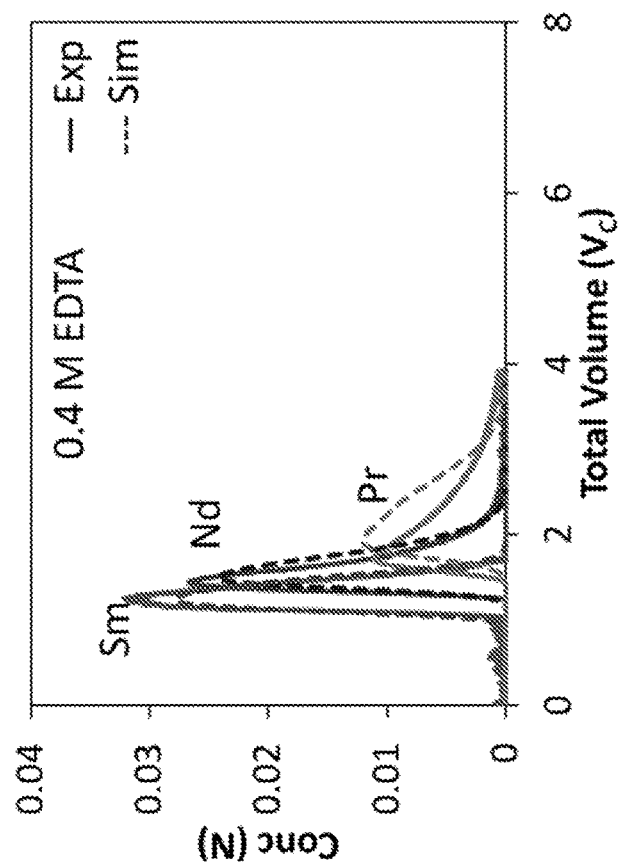
FIG. 6d shows results from isocratic elution tests at the EDTA concentration of 0.4 M for the separation of Pr, Nd, and Sm using EDTA (pH 9) as the ligand.
Figure 6C:
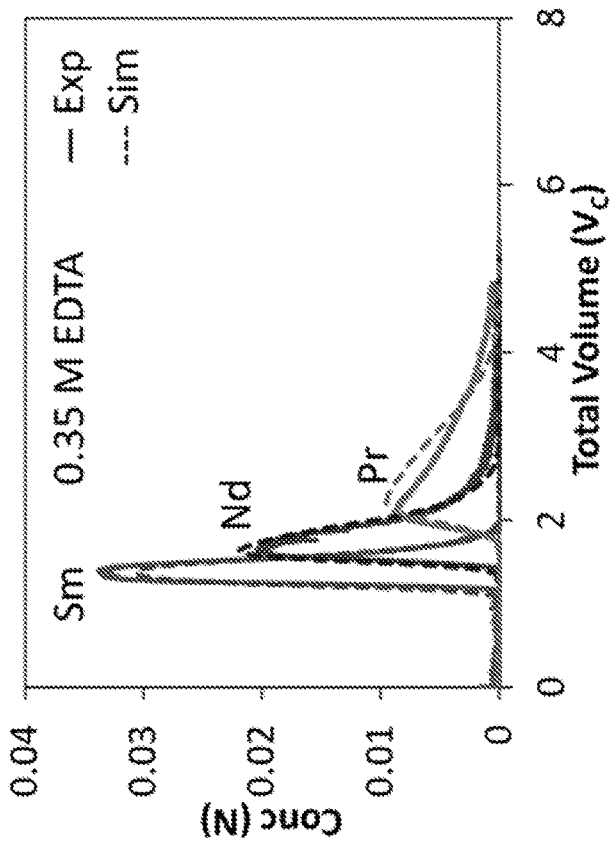
FIG. 6c shows results from isocratic elution tests at the EDTA concentration of 0.35 M for the separation of Pr, Nd, and Sm using EDTA (pH 9) as the ligand.

When the sorbent was preloaded with EDTA (0.4 M, pH 9), the slopes of the isotherm curves and the total capacities for the Ln's increased significantly (FIGS. 5c and 5d, showing the adsorption isotherms for Nd and Sm on EDTA-preloaded titania adsorbent), and the data could not be fitted well by the Langmuir model (Table 2). The results indicated that the EDTA-preloaded titania have heterogeneous sites for Ln's adsorption. Therefore, the Bi-Langmuir model was also tested and it was found to fit the data better than the Langmuir model (FIGS. 5e and 5f). The parameters showed that one type of adsorption site has high affinity but small capacity for the Ln's, whereas a second type has low affinity but large capacity (Table 2). It should be noted that data points in FIGS. 5c and 5d are the same as those in FIGS. 5e and 5f, but the fittings are based on different models. In FIGS. 5a-5d, the data are fitted by the Langmuir model, whereas in FIGS. 5e-5f, the data are fitted by the Bi-Langmuir model. The isotherm parameters obtained from the fittings are listed in Table 2.

It appears that EDTA adsorbs on the LA sites, and some of the free COO⁻ groups can serve as additional adsorption sites for the Ln's. Since the interactions between the COO⁻ groups and the Ln's are strong, the EDTA-loaded LA sites appear to be the high-affinity sites for the Ln's. The BA sites have higher affinity and capacity for the Ln's at pH 9 than at pH 5, but the affinity is still much lower than the EDTA-loaded LA sites.

Isocratic and Gradient Elution Using EDTA for Ln's Separation:

Since EDTA was found to be the most promising ligand for separating the Ln's on the titania sorbent, it was tested at different concentrations for the elution of the Ln's. The isocratic elution tests were performed at the EDTA concentrations of 0.1 M, 0.2 M, 0.35 M, and 0.4 M, and the results are shown in FIGS. 6a-6d, respectively. Specifically, FIGS. 6a-6d show the results from the isocratic elution tests for the separation of Pr, Nd, and Sm using EDTA (pH 9) as the ligand. The concentrations of EDTA are shown in each of FIGS. 6a-6d (EDTA concentration of 0.1 M in FIG. 6a; EDTA concentration of 0.2 M in FIG. 6b; EDTA concentration of 0.35 M in FIG. 6c; and EDTA concentration of 0.4 M in FIG. 6d). The solid lines were obtained from experiments and the dashed lines were obtained from simulations. The experimental conditions and the parameters used in the simulations are given in Table 1 and Table 4, respectively. When EDTA concentration was low (0.1 M), the Ln peaks were well resolved, but the product concentrations were low and the retention times were long. When EDTA concentration was high (0.4 M), the product concentrations were high but the resolution was poor.

Figure 7:
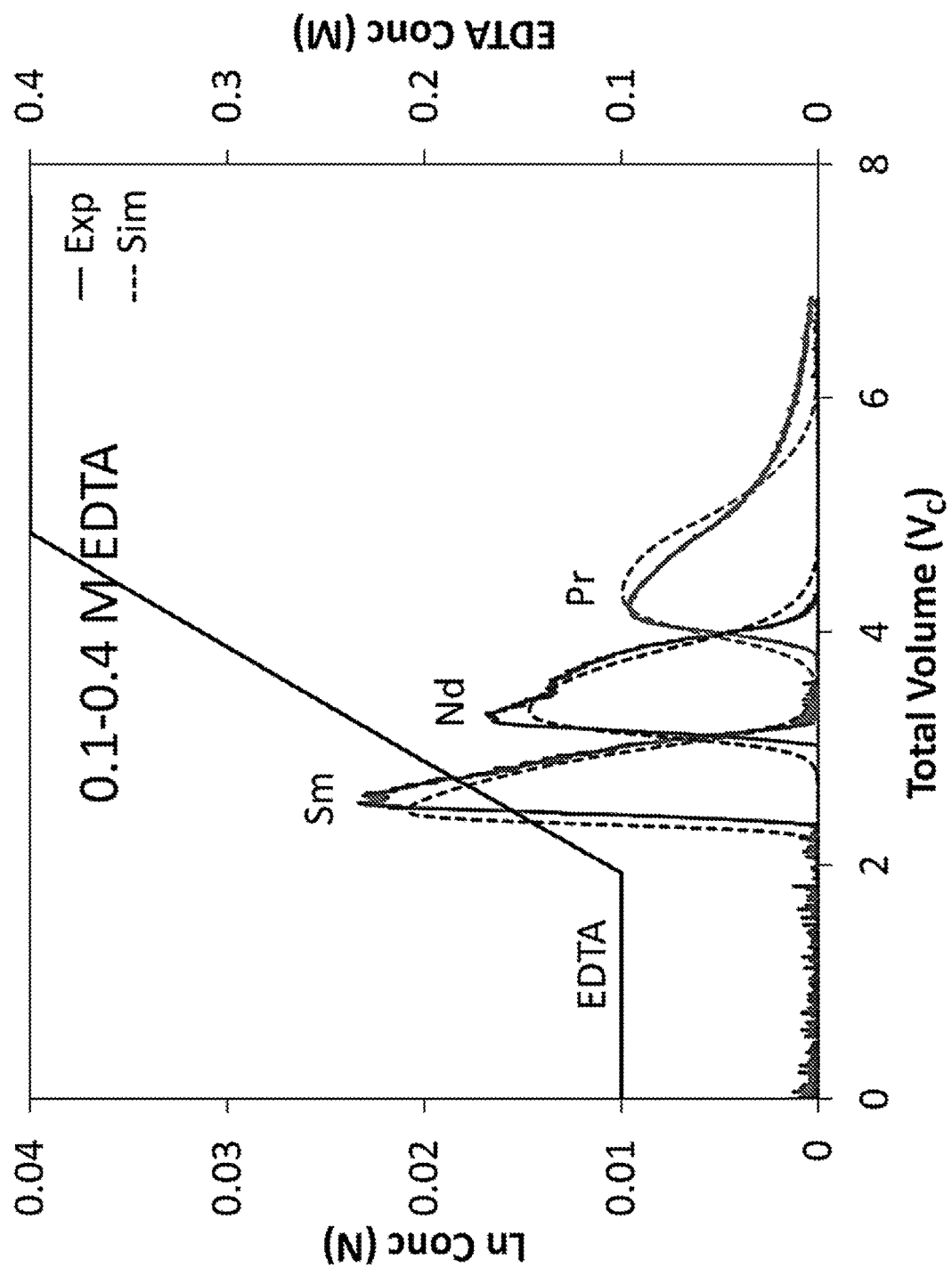
FIG. 7 shows the linear gradient elution for the separation of Pr, Nd, and Sm using EDTA (pH 9) as the ligand.

In order to achieve relatively high product concentrations without sacrificing the purities, linear gradient elution was tested for separating the Ln's. The EDTA concentration was increased from 0.1 M to 0.4 M linearly over 750 minutes, or from 1.9 $V_C$ to 4.8 $V_C$ in the effluent, FIG. 7 (specifically, FIG. 7 shows the linear gradient elution for the separation of Pr, Nd, and Sm using EDTA (pH 9) as the ligand; the concentration of EDTA increases from 0.1 M to 0.4 M; the solid lines are obtained from experiments and the dash lines are obtained from simulations; the experimental conditions and the parameters used in the simulations are given in Table 1 and Table 4, respectively; the purities and yields for each component are listed in Table 3). The elution time was similar to that of the isocratic elution with 0.2 M EDTA, but the product concentrations and the purities of the slow-moving elements (Nd and Pr) were significantly higher. As shown in Table 3, the purities and yields for all three elements were 95% or higher.

The dashed lines in FIGS. 6a-6d and 7 were obtained from VERSE simulations. The models and assumptions considered in the simulations were explained above. Since the affinity of the BA sites for the Ln's is negligible compared to the complexation of EDTA and the Ln's in the solution phase (Table 2), only the modified LA sites were considered in the simulations, and the Langmuir isotherm model was used. The ratio a(Sm):a(Nd) was lowered by 15% compared to the fitted isotherm parameters in Table 2 to match with the elution data. The ratio a(Nd):a(Pr) was kept the same as that in Table 2. The parameters used in the simulations are summarized in Table 4. The close agreement between the simulations and the experimental data supports the proposed mechanisms and the models.

TABLE 3

Purities and yields obtained in the linear gradient elution

| Lanthanide Element | Purity (%) | Yield (%) |
|---|---|---|
| Sm | 99 | 97 |
| Nd | 95 | 96 |
| Pr | 97 | 96 |

Figure 8:
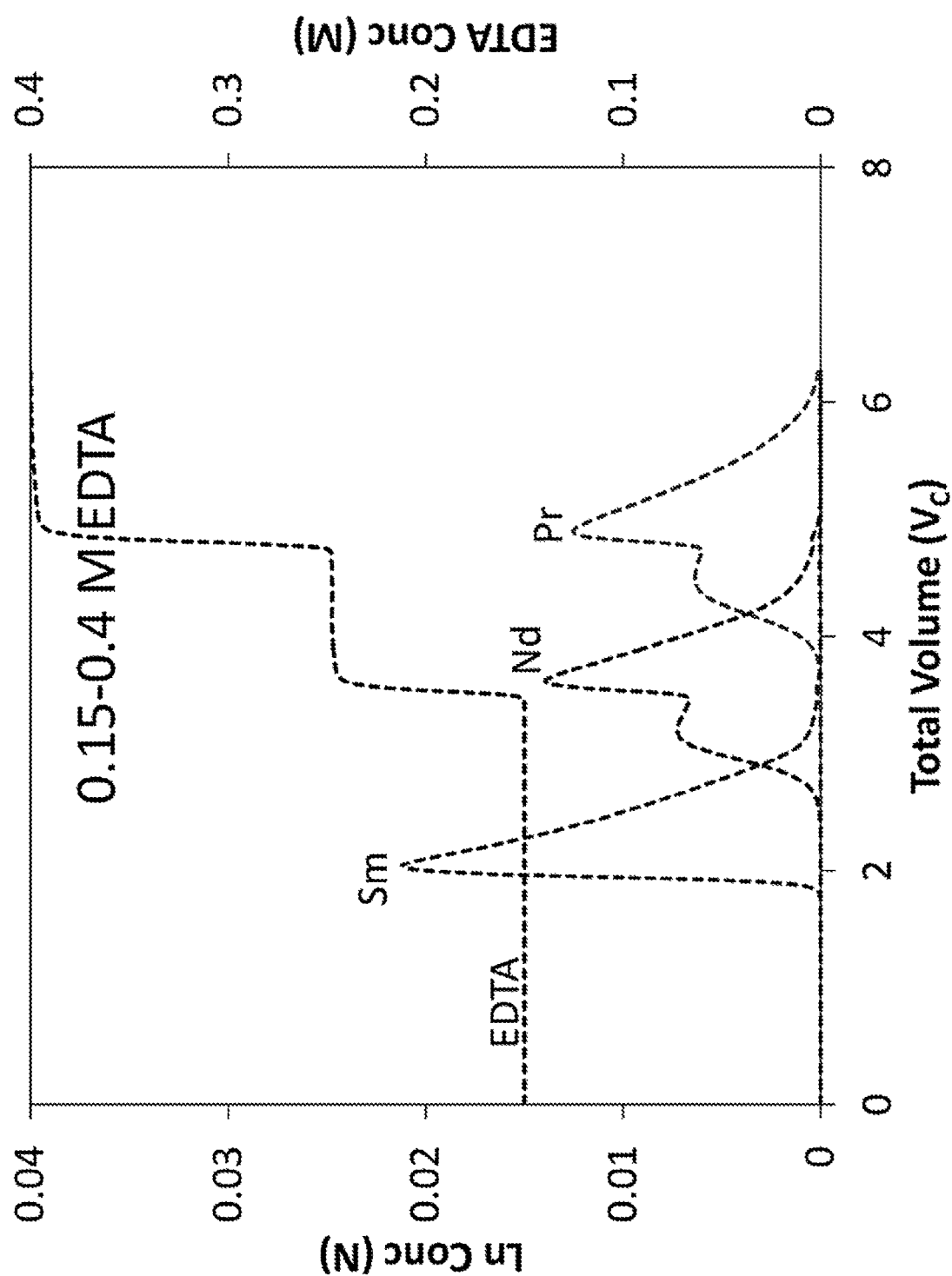
FIG. 8 shows the simulated step-wise elution process for the separation of Pr, Nd, and Sm.

A similar method to elute the Ln's with changing ligand concentration is step-wise elution, which can be applied readily to continuous separation processes. The step-wise elution of Pr, Nd and Sm from titania with increasing EDTA concentrations was simulated by VERSE as shown in FIG. 8 (specifically, FIG. 8 shows the simulated step-wise elution process for the separation of Pr, Nd, and Sm; the concentration of EDTA increases from 0.1 M to 0.25 M to 0.4 M; the parameters used in the simulations are the same as those in Table 4; the feed concentration, feed volume, and operating velocity are the same as those shown in Table 1). The parameters are the same as those in Table 4. This method is shown to be feasible for separating Ln's with high purity and high yield.

TABLE 4

Parameters used in VERSE simulations
for EDTA-assisted elution on titania

System Parameters

| L (cm) | ID (cm) | R (μm) | $\varepsilon_b$ | $\varepsilon_p$ |
|---|---|---|---|---|
| 49 | 1.16 | 40 | 0.35 | 0.4 |

Reaction Parameters

| Reaction | $k_+$ (M$^{-1}$min$^{-1}$) | $k_-$ (min$^{-1}$) | $K_C$ (M$^{-1}$) |
|---|---|---|---|
| Pr + EDTA↔PrEDTA | 250 | 2 | 125 |
| Nd + EDTA↔NdEDTA | 450 | 2 | 225 |
| Sm + EDTA↔SmEDTA | 1440 | 2 | 720 |

Isotherm Parameters (Langmuir)

| Component | a | b (M$^{-1}$) |
|---|---|---|
| Pr | 1000 | 37500 |
| Nd | 1000 | 37500 |
| Sm | 1600 | 60000 |
| NH$_4$ | 0.64 | 8 |
| others | 0 | 0 |

Mass Transfer Parameters

| Component | $D_b$ (cm$^2$/min) | $D_p$ (cm$^2$/min) | $E_b$ (cm$^2$/min) | $k_f$ (cm/min) |
|---|---|---|---|---|
| All Species | 0.0004 | 0.00004 | From Chung and Wen [19] | From Wilson and Geankoplis [20] |

Numerical Parameters

| | | Collocation Points | | Tolerance | |
|---|---|---|---|---|---|
| Axial Elements | Step Size (L/u$_0$) | Axial | Particle | Absolute (M) | Relative |
| 50 | 0.1 | 4 | 1 | 10$^{-5}$ | 10$^{-4}$ |

Figure 9:
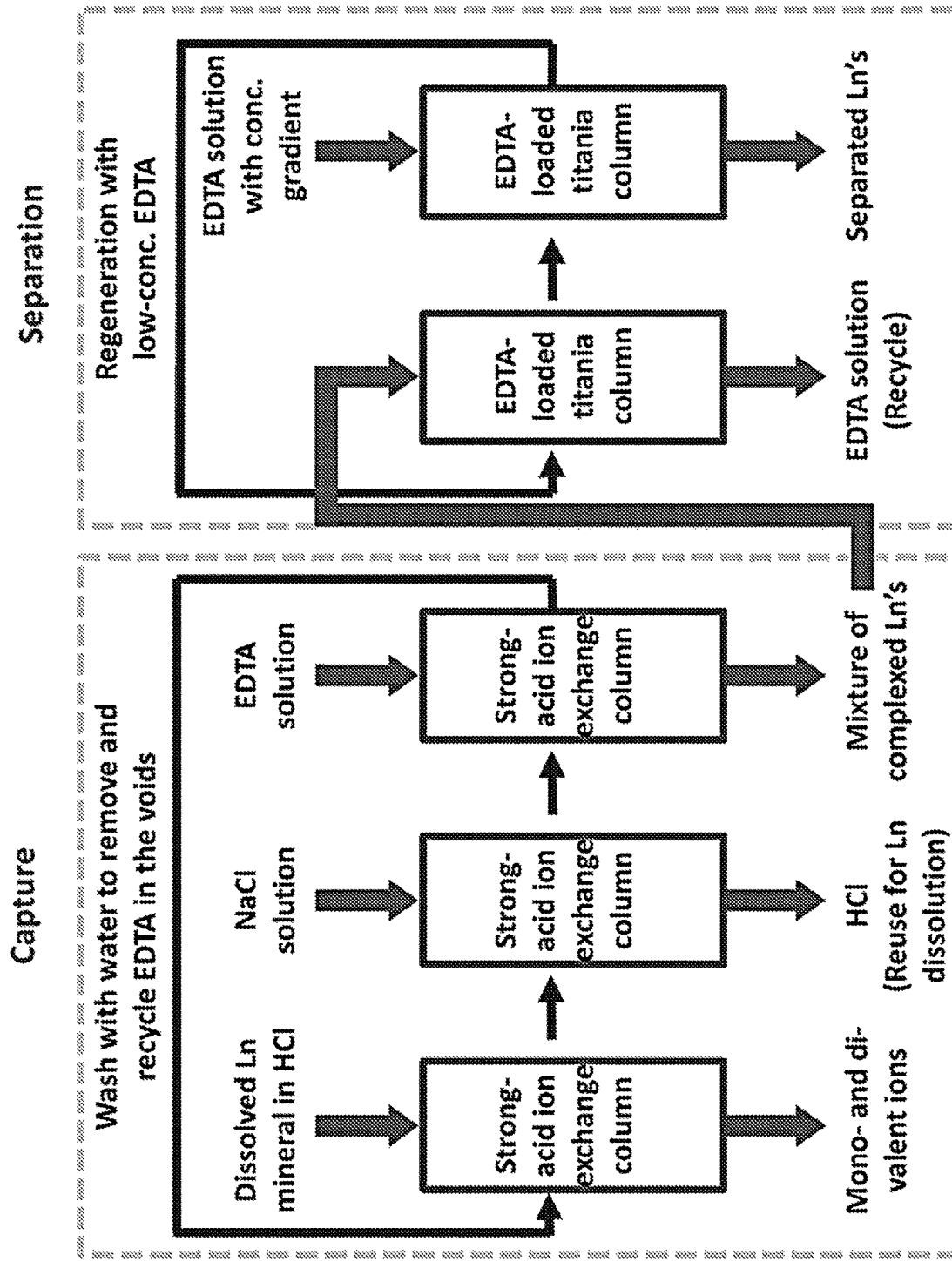
FIG. 9 shows an embodiment of large-scale production of Ln's.
Figure 10A:
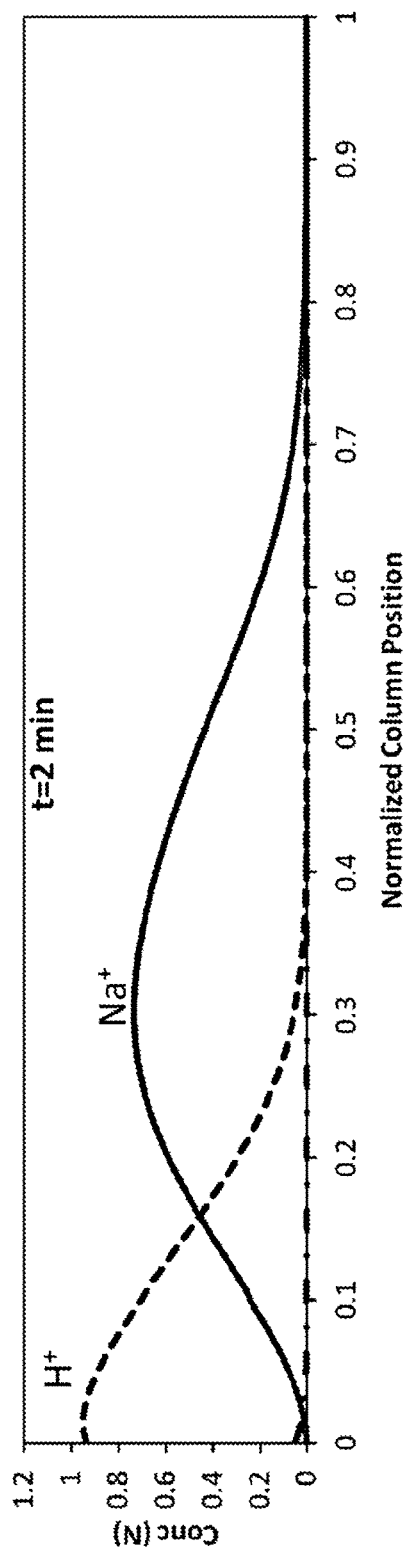
FIG. 10a shows column profiles during the feed loading (t=2 min).
Figure 10B:
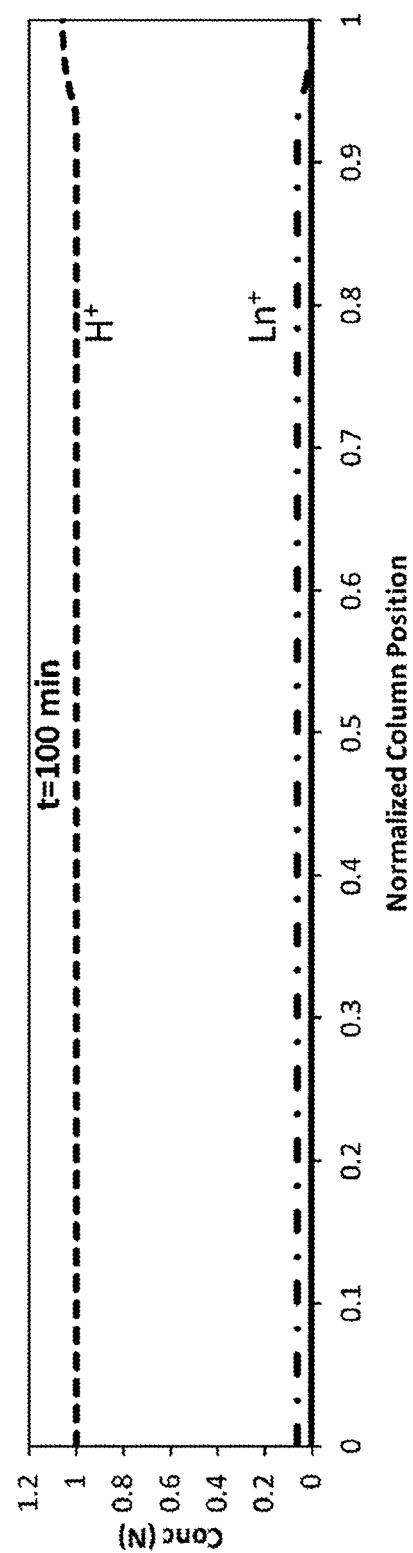
FIG. 10b shows column profiles during the feed loading (t=100 min).
Figure 10C:
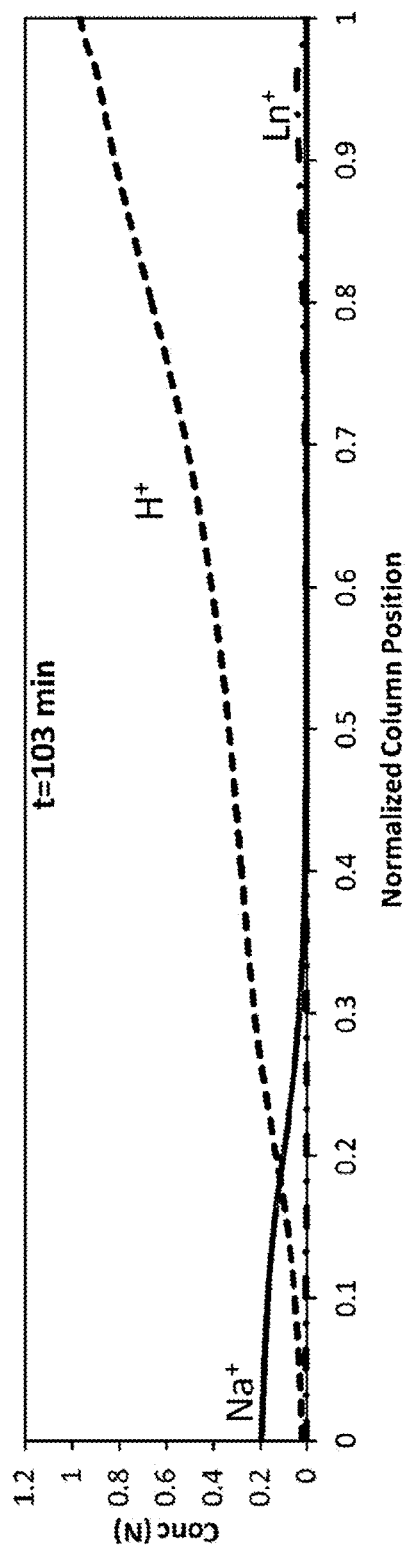
FIG. 10c shows column profiles during the Na displacement step (t=103 min).
Figure 10D:
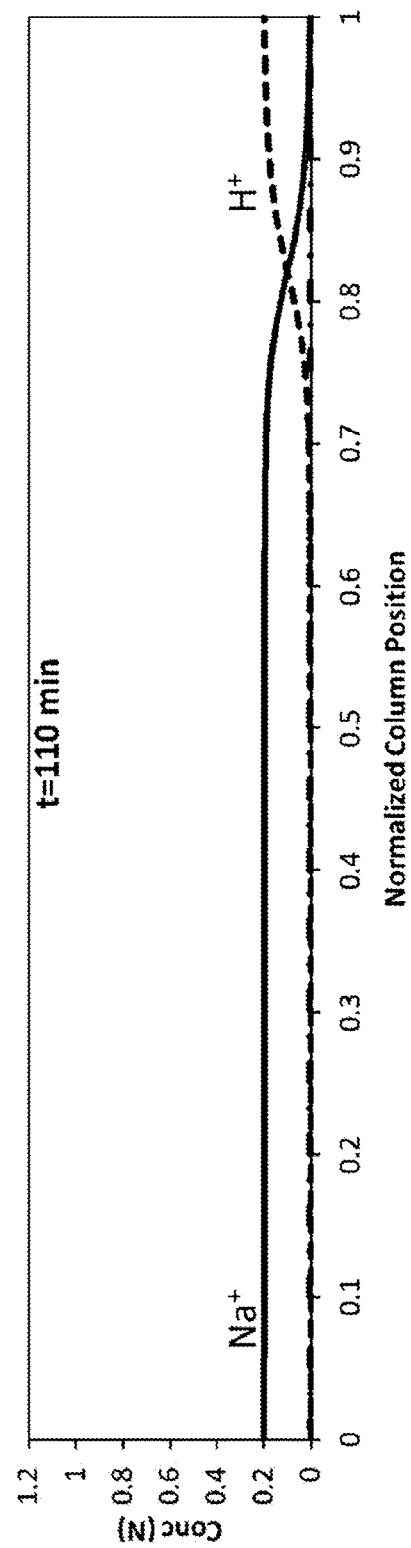
FIG. 10d shows column profiles during the Na displacement step (t=110 min).
Figure 10E:
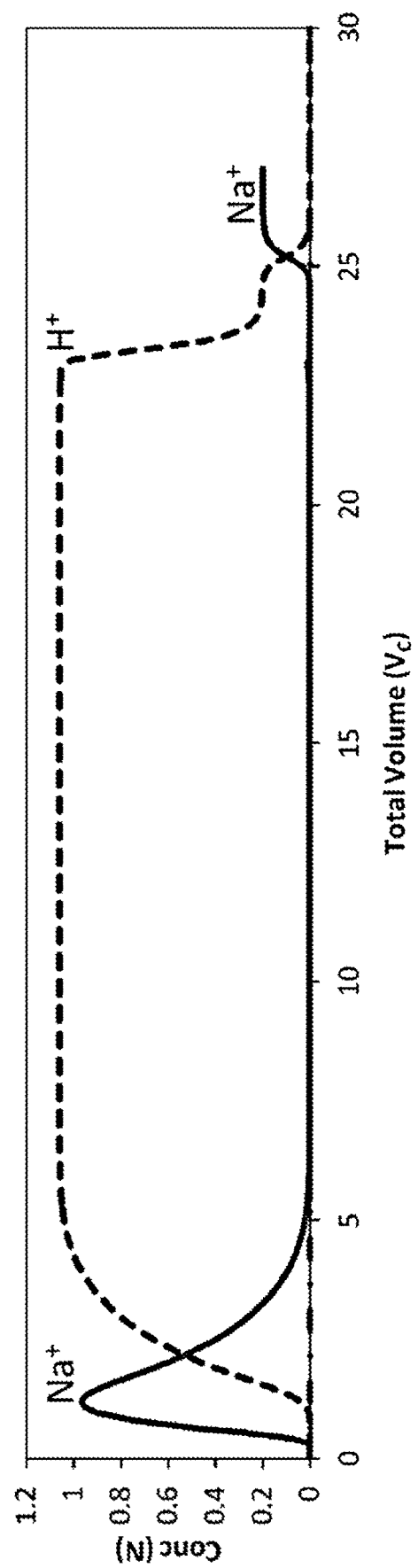
FIG. 10e shows the effluent history of the entire process including Ln capture and $Na^+$ displacement.

Large-Scale Production and Cost Analysis:

In one embodiment, the ligand-assisted elution chromatography process disclosed herein can be extended to large-scale production of Ln's. In practice, the production should have a capture step prior to the separation step, as shown in FIG. 9. The rare earth mineral separated from rocks and sands is first dissolved in a strong acid, and is loaded onto a strong-acid cation exchange column loaded with Na+. Under the strongly acidic condition, the trivalent Ln's can be captured by the ion-exchange resin, whereas most of the monovalent and divalent metal ions adsorb weakly and will pass through the column. Examples of strong-acid cation exchange resins include but are not limited to Dowex 50WX8 and Amberlite IR120. The protons remained on the resin can be displaced by a NaCl solution, which prevents precipitation of Na-form EDTA by H+ during stripping of Ln's from the ion exchange column. An example of Ln capture and NaCl displacement process was simulated as shown in FIG. 10s 10a-10e (specifically, FIGS. 10a-10e show the simulated Ln$^{3+}$ capture and Na displacement process on a cation exchange column; the column is initially Na+-loaded; the models and parameters used in the simulations are listed in Table 5; the operating velocity for loading and washing are both 1.1 cm/min; FIGS. 10a and 10b are column profiles during the feed loading (0-100 min or 0-23 V$_C$); the feed contains 0.06 N Ln$^{3+}$ and 1 N H+; FIGS. 10c and 10d are column profiles during the Na displacement step (100-120 min or 23-27 V$_C$); the Na concentration is 0.2 N; FIG. 10e is the effluent history of the entire process including Ln capture and Na displacement). The parameters used in the simulation are shown in Table 5.

TABLE 5

Parameters used in VERSE simulations for Ln
capture and NaCl wash on ion exchange resin

System Parameters

| L (cm) | ID (cm) | R (μm) | $\varepsilon_b$ | $\varepsilon_p$ |
|---|---|---|---|---|
| 5 | 1.5 | 50 | 0.35 | 0.55 |

Isotherm Parameters (Langmuir)

| Component | $K_{i\text{-}Na}^+$ (Mass Action equilibrium constant for ion exchange) |
|---|---|
| Na$^+$ | 1 |
| H$^+$ | 0.5 |
| Ln$^{3+}$ | 5 |

Mass Transfer Parameters

| Component | $D_b$ (cm$^2$/min) | $D_p$ (cm$^2$/min) | $E_b$ (cm$^2$/min) | $k_f$ (cm/min) |
|---|---|---|---|---|
| All Species | 0.001 | 0.0001 | From Chung and Wen [19] | From Wilson and Geankoplis [20] |

Numerical Parameters

| | | Collocation Points | | Tolerance | |
|---|---|---|---|---|---|
| Axial Elements | Step Size (L/u$_0$) | Axial | Particle | Absolute (M) | Relative |
| 100 | 0.1 | 4 | 1 | 10$^{-4}$ | 10$^{-3}$ |

During the feed loading step (0-100 min or 0-23 V$_C$), the concentrated H+ displaces the pre-loaded Na (FIG. 10a), and the Ln$^{3+}$ displaces the adsorbed H+ (FIG. 10b). In the displacement step (100-120 min or 23-27 V$_C$), the Ln's adsorbed strongly on the resin so that the peak in the bulk phase shrinks rapidly (FIG. 10c). The remaining H+ adsorbed on the resin is displaced by the Na (FIG. 10d) and is eventually cleared out from the column. No leakage of Ln's occurs over the entire loading and displacement processes (FIG. 10e).

The captured Ln's are then eluted by Na-form EDTA, and loaded onto a EDTA-preloaded titania column. A gradient of EDTA concentration will be used to elute the adsorbed Ln's from the titania column. A well-designed gradient elution can achieve high-yield and high-purity separation for all the Ln's. Compared to the ligand-assisted displacement chromatography, the ligand-assisted elution chromatography process is more productive. More importantly, the latter does not need harsh or expensive chemicals for column regeneration, leading to a lower production cost.

Figure 11A:
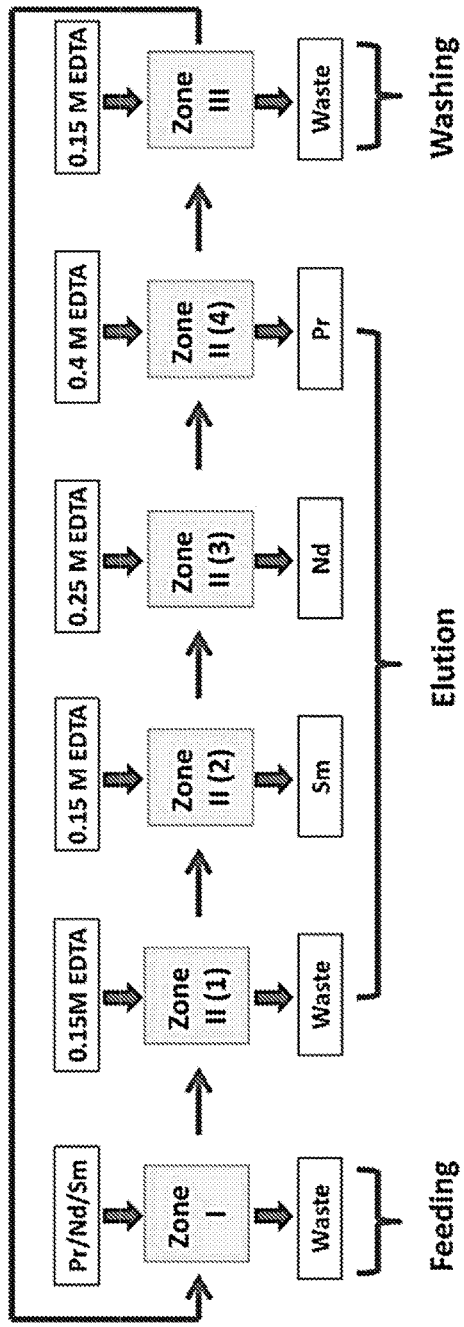
FIG. 11a shows the continuous counter-current chromatography processes for the separation of 3 Ln elements.
Figure 11B:
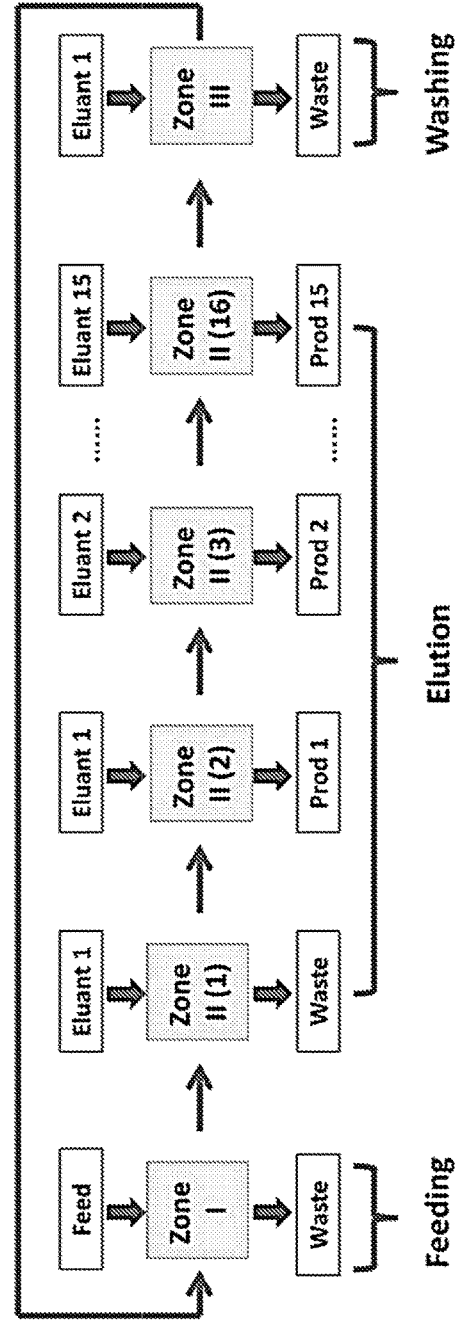
FIG. 11b shows the continuous counter-current chromatography processes for the separation of 15 lanthanides or metal ions.

A continuous counter-current chromatography process can be used to increase the productivity and reduce the cost of Ln's separation. FIGS. 11a and 11b show the continuous counter-current chromatography processes for the separation of 3 Ln elements (FIGS. 11a) and 15 Ln elements (FIG. 11b). Eluant 1-15 are EDTA solutions with increasing concentrations, and Prod 1-15 are different Ln elements. The effluents collected in the waste tanks are EDTA solutions, which can be recycled and reused. An entire cycle for ternary separation contains three major zones: feeding, elution, and washing (FIG. 11a). In the feeding zone, the Ln mixture is loaded onto the column. In the elution zone, different Ln's can be eluted at different EDTA concentrations. In the washing zone, the column is flushed by a diluted EDTA solution. The concentrated EDTA solution in the effluent can be collected and reused. After the washing step, the next cycle will start with the feeding step. Since EDTA has significant selectivity for all adjacent Ln pairs (Table 6), the separation process in FIG. 11a can also be extended to 15 elements, as shown in FIG. 11b.

As an example demonstrative of the method disclosed herein, a preliminary cost analysis was conducted for the production of Ln's based on the following assumptions: (1) The production scale is 20,000 metric tons (m.t) per year, which is the annual capacity claimed by MolyCorp, the major Ln production company in the United States; (2) The production time is 320 days per year; (3) The price for a single unit is 300,000 for batch process, and 1,000,000 for continuous process, with a depreciation of 10 years; (4) The column size is 3 m L×4.5 m ID; (5) The costs of chemicals (market price in China, May 2014) are EDTA-2,000/m.t, sorbent-1,000/m.t (life time-10 years), HCl—200/m.t, NaCl-100/m.t, oxalic acid-700/m.t, and the cost of water (market price in USA) is 0.5/m.t; (6) The excess chemicals used in dissolution (HCl) and Ln precipitation (oxalic acid) can be recycled; (7) The total feed concentration of Ln's is 0.06 N, and the residence time L/u, for the feed loading is 250 min, the same as those used in our experimental tests (FIGS. 6a-6d and 7). The cost estimations for batch and continuous processes are shown in Table 7. It is noteworthy that if 99% of the EDTA can be recycled, the production cost is estimated to be 3.4 per kilogram, which is lower than the current production cost in China, 5.6/kg, and in Australia, 10.1/kg.

The estimated cost for ligand-assisted elution is based on EDTA at pH 9. Optimization of the pH of EDTA may reduce the cost to below 3.4/kg.

TABLE 6

Selectivity of EDTA for adjacent Ln's

| Ln pairs | $\alpha_{EDTA}$ |
|---|---|
| Ce—La | 3.7 |
| Pr—Ce | 2.5 |
| Nd—Pr | 1.8 |
| Pm—Nd | $\alpha_{EDTA}$(Sm—Nd) = 3.2 |
| Sm—Pm | |
| Eu—Sm | 1.5 |
| Gd—Eu | 1.05 |
| Tb—Gd | 4.2 |
| Dy—Tb | 2.3 |
| Ho—Dy | 2.6 |
| Er—Ho | 1.8 |
| Tm—Er | 3.1 |
| Yb—Tm | 1.8 |
| Lu—Yb | 1.9 |

TABLE 7

Preliminary estimations of production costs

| | | Batch | | Continuous | |
|---|---|---|---|---|---|
| | | 95% EDTA Recycle | 99% EDTA Recycle | 95% EDTA Recycle | 99% EDTA Recycle |
| Dissolution Cost (The excess acid is assumed to be recycled) ($/kg) | | 0.3 | 0.3 | 0.3 | 0.3 |
| Capture and Salt Washing Cost ($/kg) | | 0.2 | 0.2 | 0.2 | 0.2 |
| Separation Cost ($/kg) | Chemical ($/kg) | 22.9 | 6.1 | 7.6 | 2 |
| | Sorbent ($/kg) | 0.3 | 0.3 | 0.1 | 0.1 |
| | Equip ($/kg) | 1.3 | 1.3 | 0.1 | 0.1 |
| Precipitation Cost ($/kg) | | 0.7 | 0.7 | 0.7 | 0.7 |
| Total ($/kg) | | 25.7 | 8.9 | 9.0 | 3.4 |

CONCLUSIONS

A ligand-assisted elution chromatography process has been developed for the separation of Ln's. The mechanism of Ln separation in the presence of a ligand has been studied. The Ln's can be well separated only if the overall selectivity, which approximates the ratio of the ligand selectivity to the sorbent selectivity, is significantly greater than 1, and the dimensionless complexation equilibrium constant $K_C[L]$ and the Langmuir a value are in the same order of magnitude ($K_C[L]/a \sim 1$).

Based on the analysis, several ligands have been tested, among which EDTA was found to be the best ligand for separating the Ln's on a titania column. The process was demonstrated by a ternary separation of Pr, Nd, and Sm. Pure products of each element were obtained under well-designed ligand concentrations. In order to concentrate the products and shorten the cycle time, linear-gradient elution was used, and the purities and yields for all three elements were greater than 95%. Rate model simulations taking into account adsorption, mass transfer, and reactions were used to verify the proposed mechanisms and to elucidate the dynamics of ligand-assisted separation. The effluent histories obtained from the simulations agreed closely with the experimental data.

As mentioned above, the processes herein disclosed can be extended to separate other lanthanides or other species with similar properties, including other rare earth elements or other metal ions. For large-scale production, economical continuous processes can be used for metal ion separation to increase the productivity and lower the cost. A preliminary cost estimation for rare earth element separation, for example, shows that if most of the ligand (99%) is recycled and reused, the ligand-assisted elution chromatography processes are environmentally benign and less costly than the current solvent extraction processes.

Those skilled in the art will recognize that numerous modifications can be made to the specific implementations described above. The implementations should not be limited to the particular limitations described. Other implementations may be possible.

The invention claimed is:
1. A process for isolating a substantially pure (95% or higher) rare earth element (REE) comprising the steps of:
   a. dissolving a mixture containing REEs in a strong acid to result in a dissolved mixture of metal ions, including that of REEs;

b. capturing metal ions of REEs in a first set of chromatographic columns comprising strong acid cation exchange resins;

c. washing said first set of chromatographic columns with a salt solution to remove non-adsorbing metal ions;

d. eluting metal ions of REES from said first set of chromatographic columns with a first ligand solution to result in a solution of enriched metal ions of REEs;

e. loading said solution of enriched metal ions of REEs onto a second set of chromatographic columns; and f. eluting bound metal ions of REEs stepwise from said second set of chromatographic columns using a second ligand solution to afford a substantially pure REE, wherein said second set of chromatographic columns comprising hydrous polyvalent metal oxide selected from the group consisting of $TiO_2$, $ZrO_2$, or $SnO_2$ and wherein ligand of said second ligand solution coordinates with said hydrous polyvalent metal oxide.

2. The process of claim 1 wherein said salt solution is a sodium or ammonium salt solution with a counter ion selected from the group consisting of chloride ($Cl^-$), sulfate ($SO_4^{2-}$), bisulfate ($HSO_4^-$), and nitrate ($NO_3^-$).

3. The process of claim 1 wherein said first ligand is ethylenediaminetetraacetic acid (EDTA), pentetic acid (DTPA), 1,2-diaminocyclohexanetetraacetic acid (DCTA), N-(2-Hydroxyethyl) ethylenediamine-N,N',N'-triacetic acid (HEDTA), iminodiacetic acid (IDA), citric acid, or any combination thereof.

4. The process of claim 1, wherein said metal ions of REEs are eluted separately by using said first ligand solution with a linear or stepwise concentration gradient of said ligand.

5. The process of claim 1, wherein said metal ions of REEs are eluted separately by using said first ligand solution with a linear or stepwise gradient of pH.

6. The process of claim 1, wherein said second ligand solution is a solution of ethylenediaminetetraacetic acid (EDTA), pentetic acid (DTPA), 1,2-diaminocyclohexanetetraacetic acid (DCTA), N-(2-Hydroxyethyl) ethylenediamine-N,N',N'-triacetic acid (HEDTA), iminodiacetic acid (IDA), citric acid, or any combination thereof.

7. The process of claim 6, wherein metal ions of REEs are eluted separately by using said second ligand solution with a linear or stepwise concentration gradient of said ligand.

8. The process of claim 6, wherein metal ions of REEs are eluted separately by using said second ligand solution with a linear or stepwise gradient of pH.

9. The process of claim 1, wherein said strong acid compromises one or more acids selected from the group consisting of hydrochloric acid (HCl), sulfuric acid ($H_2SO_4$), and nitric acid ($HNO_3$).

10. The process of claim 1, wherein said REEs comprise at least one of praseodymium (Pr), neodymium (Nd), and samarium (Sm).

11. The process of claim 1, wherein said chromatographic separation process is performed at a pH from about 3 to about 11 with a said first or second ligand concentration of from about 0.001 M to about 1 M.

* * * * *